United States Patent
Bornzin et al.

(10) Patent No.: US 12,042,658 B2
(45) Date of Patent: Jul. 23, 2024

(54) BIOSTIMULATOR HAVING LOW-POLARIZATION ELECTRODE(S)

(71) Applicant: Pacesetter, Inc., Sylmar, CA (US)

(72) Inventors: Gene A. Bornzin, Santa Monica, CA (US); Wesley Alleman, Santa Clarita, CA (US); Tyler J. Strang, Valencia, CA (US); Keith Victorine, Valencia, CA (US); Nicole Cooper, Burbank, CA (US)

(73) Assignee: PACESETTER, INC., Sylmar, CA (US)

( * ) Notice: Subject to any disclaimer, the term of this patent is extended or adjusted under 35 U.S.C. 154(b) by 19 days.

(21) Appl. No.: 17/199,260

(22) Filed: Mar. 11, 2021

(65) Prior Publication Data

US 2021/0308472 A1  Oct. 7, 2021

Related U.S. Application Data

(60) Provisional application No. 63/003,596, filed on Apr. 1, 2020.

(51) Int. Cl.
*A61N 1/37* (2006.01)
*A61N 1/05* (2006.01)
(Continued)

(52) U.S. Cl.
CPC ......... *A61N 1/3712* (2013.01); *A61N 1/0573* (2013.01); *A61N 1/3714* (2013.01);
(Continued)

(58) Field of Classification Search
CPC . A61N 1/3714; A61N 1/37512; A61N 1/3756
See application file for complete search history.

(56) References Cited

U.S. PATENT DOCUMENTS

| 6,430,447 B1 | 8/2002 | Chitre et al. |
| 8,541,131 B2 | 9/2013 | Lund et al. |

(Continued)

FOREIGN PATENT DOCUMENTS

| EP | 3290081 A1 | 7/2018 |
| WO | 2016011042 A1 | 1/2016 |

OTHER PUBLICATIONS

Extended European Search Report from related EP Application No. 21163601.4 mailed on Aug. 20, 2021 (6 pages).
(Continued)

*Primary Examiner* — William J Levicky
(74) *Attorney, Agent, or Firm* — WOMBLE BOND DICKINSON (US) LLP

(57) ABSTRACT

A biostimulator, such as a leadless pacemaker, having electrode(s) coated with low-polarization coating(s), is described. A low-polarization coating including titanium nitride can be disposed on an anode, and a low-polarization coating including a first layer of titanium nitride and a second layer of platinum black can be disposed on a cathode. The anode can be an attachment feature used to transmit torque to the biostimulator. The cathode can be a fixation element used to affix the biostimulator to a target tissue. The low-polarization coating(s) impart low-polarization to the electrode(s) to enable an atrial evoked response to be detected and used to effect automatic output regulation of the biostimulator. Other embodiments are also described and claimed.

20 Claims, 12 Drawing Sheets

(51) Int. Cl.
  *A61N 1/375* (2006.01)
  *A61N 1/378* (2006.01)
(52) U.S. Cl.
  CPC ....... *A61N 1/3716* (2013.01); *A61N 1/37512* (2017.08); *A61N 1/3756* (2013.01); *A61N 1/378* (2013.01); *A61N 2001/0578* (2013.01); *A61N 2001/058* (2013.01)

(56) References Cited

U.S. PATENT DOCUMENTS

| | | |
|---|---|---|
| 9,393,427 B2 | 7/2016 | Schmidt et al. |
| 10,004,907 B2 | 6/2018 | Bornzin |
| 2005/0049665 A1 | 3/2005 | Brabec et al. |
| 2006/0122682 A1 | 6/2006 | Sommer et al. |
| 2011/0077708 A1 | 3/2011 | Ostroff |
| 2012/0116489 A1 | 5/2012 | Khairkhahan et al. |
| 2013/0116740 A1 | 5/2013 | Bornzin et al. |
| 2013/0274847 A1 | 10/2013 | Ostroff |
| 2013/0324825 A1 | 12/2013 | Ostroff et al. |
| 2015/0025612 A1 | 1/2015 | Haasl et al. |
| 2015/0051615 A1* | 2/2015 | Schmidt ............... A61N 1/3756 606/129 |
| 2015/0057721 A1 | 2/2015 | Stahmann et al. |
| 2015/0238768 A1* | 8/2015 | Bornzin ............... A61N 1/3756 607/28 |
| 2017/0105635 A1* | 4/2017 | Cho ..................... A61N 1/3756 |
| 2018/0078775 A1 | 3/2018 | Linder et al. |
| 2018/0140850 A1* | 5/2018 | Linder ................. A61N 1/3756 |
| 2019/0054304 A1* | 2/2019 | Maile ................... A61N 1/3756 |
| 2019/0275340 A1 | 9/2019 | Eby et al. |
| 2020/0289835 A1 | 9/2020 | Eby et al. |

OTHER PUBLICATIONS

USPTO Notice of Allowance from related U.S. Appl. No. 17/199,266 mailed on Feb. 1, 2023 (9 pages).

Extended European Search Report from related EP Application No. 23219269.0 mailed on Mar. 28, 2024 (6 pages).

\* cited by examiner

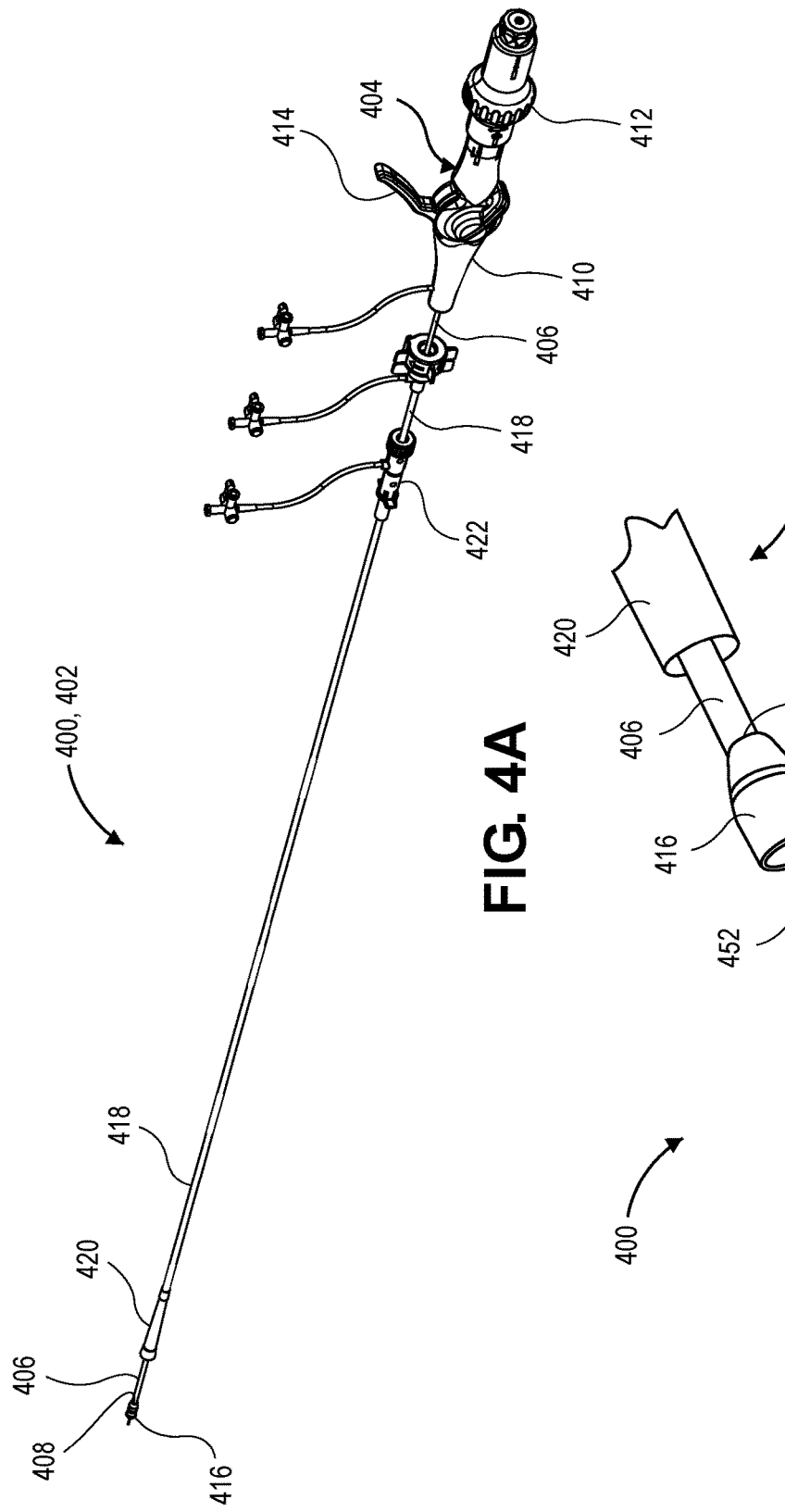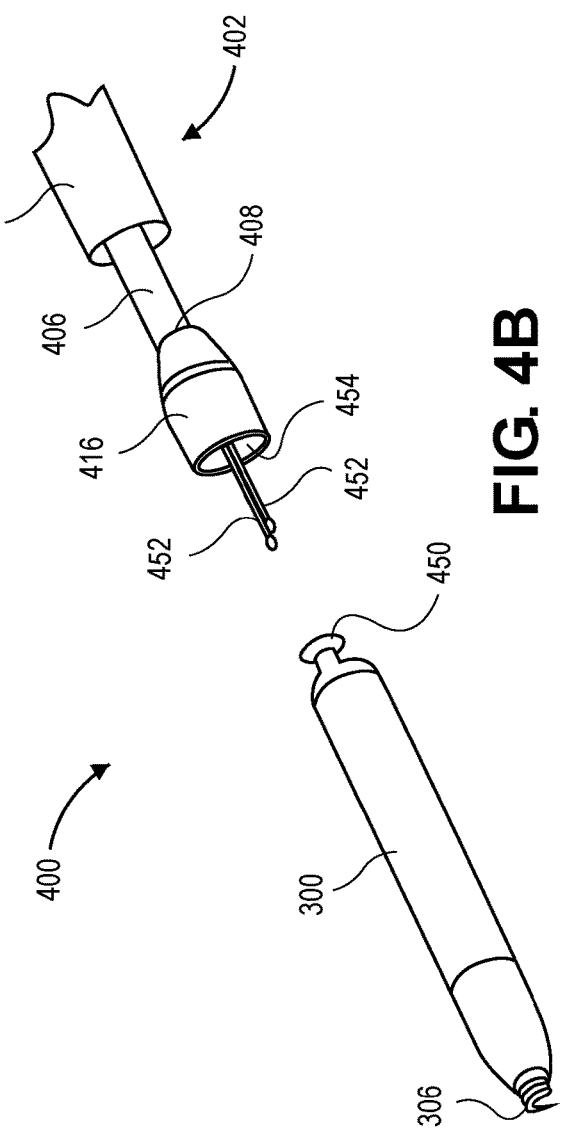

BIOSTIMULATOR HAVING LOW-POLARIZATION ELECTRODE(S)

This application claims the benefit of priority of U.S. Provisional Patent Application No. 63/003,596, filed on Apr. 1, 2020, which is incorporated herein by reference in its entirety to provide continuity of disclosure.

BACKGROUND

Field

The present disclosure relates to biostimulators. More specifically, the present disclosure relates to leadless biostimulators.

Background Information

Cardiac pacing by an artificial pacemaker provides electrical stimulation of a heart when a natural pacemaker and/or conduction system of the heart fails to provide synchronized atrial and ventricular contractions at rates and intervals sufficient for a patient's health. Cardiac pacing by conventional pacemakers is usually performed by a pulse generator implanted subcutaneously or sub-muscularly in or near a patient's pectoral region, which delivers an electrical impulse to the heart via an elongated electrical lead implanted therein. Well known difficulties exist for conventional pacemakers, such as complex lead connectors and/or risks of mechanical failure of the leads. As a result, leadless cardiac pacemakers have been developed.

Leadless cardiac pacemakers are self-contained and self-sustainable biostimulators that can be attached to tissue within a dynamic environment. For example, leadless cardiac pacemakers can be implanted in chambers of the heart to deliver pacing pulses to target tissue in an atrium or ventricle of the heart. Leadless cardiac pacemakers contain batteries to supply energy of the pacing pulses. A capacity of the batteries is limited by a size of the leadless cardiac pacemaker. Furthermore, a small size of the leadless pacemaker is needed to allow the leadless pacemaker to be delivered intravenously and to reside within the heart chamber.

SUMMARY

The limitations imposed on the battery capacity of a leadless cardiac pacemaker by the device size requirements dictates that power consumption of the leadless cardiac pacemaker should be minimized in order to maximize pacer longevity. Existing leadless cardiac pacemakers implement "autocapture" to minimize power consumption. Autocapture is performed by the leadless cardiac pacemaker when the device determines a pacing output at which capture of the target chamber, e.g., an atrium, is lost, and then sets a stimulus amplitude to the threshold plus a safety margin. Autocapture allows for effective pacing with minimal battery current drain, and thus, prolonged pacer longevity. Successful implementation of autocapture, however, presumes that the leadless pacemaker can determine the capture threshold by detecting the chamber evoked response, which is consistent with chamber capture. Thus, the leadless cardiac pacemaker must be able to accurately detect the chamber evoked response to successfully implement autocapture.

Detection of the chamber evoked response can be complicated by the small amplitude of the chamber evoked response. More particularly, polarization of the pacemaker electrodes during pacing can cause a decaying polarization potential that superimposes on and obscures the chamber evoked response. Complex signal discrimination techniques, such as frequently executed correlations, may be used to improve detection of the chamber evoked response despite the polarization of the pacemaker electrodes. Such techniques, however, require substantial processing power and are themselves a burden on battery current drain. Accordingly, existing leadless pacemakers that experience polarization of the pacemaker electrodes may not reliably perform autocapture, particularly in target chambers having low chamber evoked responses, such as the atria.

A biostimulator, e.g., a leadless cardiac pacemaker, having an electrode coated by a low-polarization coating is described below. In an embodiment, the biostimulator has a battery assembly including a cell can containing an electrolyte, and an attachment feature is connected to the battery assembly. The attachment feature can be used to transmit torque to the biostimulator. Accordingly, the attachment feature includes a stem having an annular stem wall that extends between a base that connects to the battery assembly and a button that receives the torque. A low-polarization coating is disposed on an exterior surface of the attachment feature to impart low-polarization to the attachment feature, which may be an anode of the biostimulator. Accordingly, the coated attachment feature can enable an atrial evoked response to be detected and used to effect automatic output regulation of the biostimulator.

The low-polarization coating can include titanium nitride and/or iridium oxide. In an embodiment, the low-polarization coating covers an entirety of the exterior surface of the attachment feature. The attachment feature can have an interior surface, and the low-polarization coating may cover only a portion of the interior surface.

The biostimulator components may have other notable characteristics. The attachment feature can be coupled to the battery assembly by a weld that extends circumferentially around the base and the cell can. The cell can may also be at least partly covered by an insulating coating. The attachment feature may be monolithically formed from a rigid material, and the stem can be a single post having an annular transverse profile. These characteristics and others described below can contribute to the biostimulator being capable of detecting an atrial evoked response, and using the atrial evoked response to effect automatic output regulation.

Biostimulator systems including the biostimulator are also described. For example, a biostimulator system can include a transport system including a catheter having a distal end, and the biostimulator may be connected to the distal end.

Methods of manufacturing the biostimulator are also described. In an embodiment, the low-polarization coating is disposed on the exterior surface of the attachment feature, and the attachment feature is mounted on the battery assembly.

The above summary does not include an exhaustive list of all aspects of the present invention. It is contemplated that the invention includes all systems and methods that can be practiced from all suitable combinations of the various aspects summarized above, as well as those disclosed in the Detailed Description below and particularly pointed out in the claims filed with the application. Such combinations have particular advantages not specifically recited in the above summary.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIGS. 4A-4B are perspective views of a biostimulator delivery system, in accordance with an embodiment.

DETAILED DESCRIPTION

Figure 1:
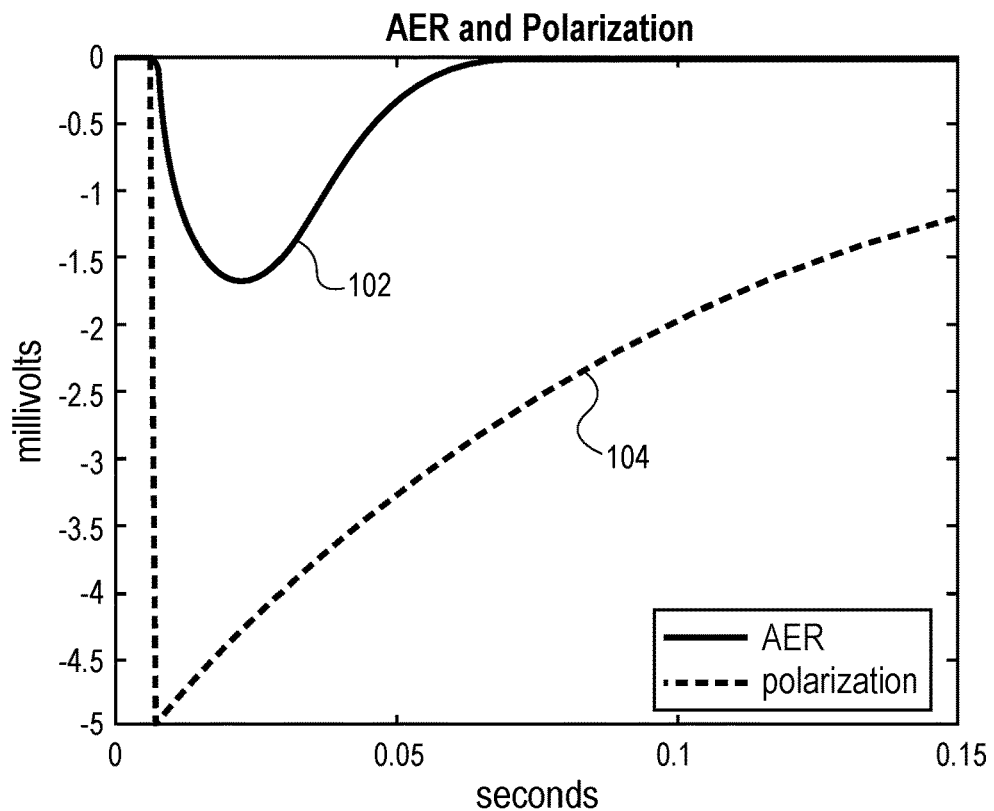
FIG. 1 is a graph of atrial evoked response and electrode polarization waveforms, in accordance with an embodiment.

Embodiments describe a biostimulator having electrode(s) coated with low-polarization coating(s). The biostimulator may be a leadless biostimulator, such as a leadless cardiac pacemaker used to pace cardiac tissue. The biostimulator may, however, be used in other applications, such as deep brain stimulation. Thus, reference to the biostimulator as being a cardiac pacemaker is not limiting. Furthermore, reference to the biostimulator as being used to detect an atrial evoked response is not to be limiting of the applications of the biostimulator because the biostimulator may be used to detect other tissue or chamber evoked responses, such as a ventricular evoked response. More particularly, the biostimulator may be implanted in an atrium, a ventricle, or another body tissue of a heart.

In various embodiments, description is made with reference to the figures. However, certain embodiments may be practiced without one or more of these specific details, or in combination with other known methods and configurations. In the following description, numerous specific details are set forth, such as specific configurations, dimensions, and processes, in order to provide a thorough understanding of the embodiments. In other instances, well-known processes and manufacturing techniques have not been described in particular detail in order to not unnecessarily obscure the description. Reference throughout this specification to "one embodiment," "an embodiment," or the like, means that a particular feature, structure, configuration, or characteristic described is included in at least one embodiment. Thus, the appearance of the phrase "one embodiment," "an embodiment," or the like, in various places throughout this specification are not necessarily referring to the same embodiment. Furthermore, the particular features, structures, configurations, or characteristics may be combined in any suitable manner in one or more embodiments.

The use of relative terms throughout the description may denote a relative position or direction. For example, "distal" may indicate a first direction along a longitudinal axis of a biostimulator. Similarly, "proximal" may indicate a second direction opposite to the first direction. Such terms are provided to establish relative frames of reference, however, and are not intended to limit the use or orientation of a biostimulator to a specific configuration described in the various embodiments below.

In an aspect, a biostimulator includes a coating on an anode to impart low-polarization to the anode. The low-polarization coating can be a titanium nitride or iridium oxide coating, for example. In an embodiment, the anode is an attachment feature of the biostimulator used to capture and transmit torque to the biostimulator. The low-polarization anode can improve atrial evoked response sensing for atrial autocapture. More particularly, the coated anode enables atrial evoked response detection to effect automatic output regulation of the biostimulator.

In an aspect, a biostimulator includes a coating on a cathode to impart low-polarization to the cathode. The low-polarization coating can be a dual-layer coating including a first layer having titanium nitride and a second layer having platinum black. The first layer can be a base layer of titanium nitride and the second layer can be formed by platinization of the base layer, for example. In an embodiment, the cathode is a fixation element of the biostimulator used to attach the biostimulator to a target tissue. The coated and platinized cathode may be used in combination with a low-polarization anode. For example, a low-polarization coating can be applied to the anode of the biostimulator, as described above. The low-polarization cathode and/or anode can improve atrial evoked response sensing for atrial autocapture. More particularly, the coated electrode(s) enable atrial evoked response to effect automatic output regulation of the biostimulator.

Figure 2:
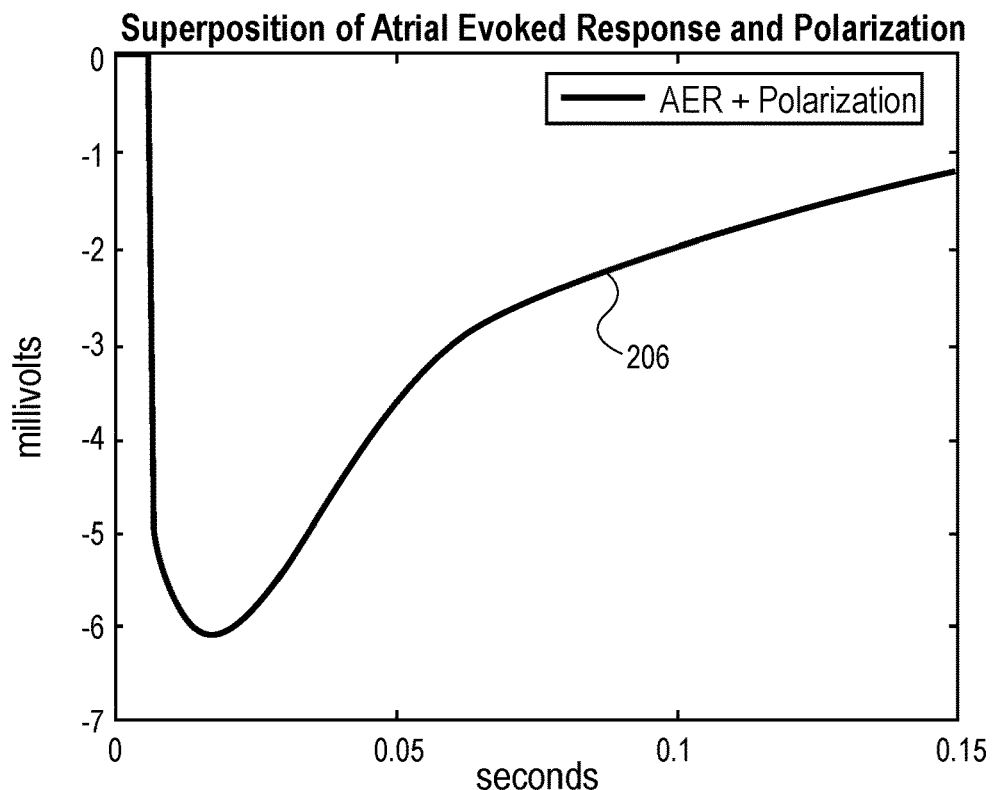
FIG. 2 is a graph of an atrial evoked response waveform superimposed on an electrode polarization waveform, in accordance with an embodiment.

FIGS. 1-2 illustrate how polarization of electrodes can negatively impact the ability of a biostimulator to detect chamber evoked response. Referring to FIG. 1, a graph of atrial evoked response and electrode polarization waveforms is shown in accordance with an embodiment. A chamber evoked response, e.g., in this case an atrial evoked response 102, occurs in response to pacing from a biostimulator. For example, the biostimulator can deliver a pacing impulse of between 0.5 to 1.5 volts over a period of 0.4 ms to capture the atrium. When the biostimulator delivers the pacing impulse to the atrium, a wave of excitation moves across the atrium and during that time the tissue has a latency and then depolarizes before contracting. The negative depolarization of the cells is the atrial evoked response 102 and has a magnitude of a few millivolts and a duration of about 50 ms or less, for example.

When current is passed through the cathode of the biostimulator to the anode of the biostimulator during pacing, the electrode-electrolyte interface behaves like a capacitor and charges up to tens or hundreds of millivolts. After delivery of the atrial pacing pulse, there is an 8 ms time delay during which the biostimulator blanks sensing while the pacing pulse is delivered and the pacing capacitor recharge takes place. The recharge occurs over a period of about 7 ms and drives current through the electrode system, e.g., the cathode and the anode of the biostimulator, in a direction that cancels some of the polarization that accumulates at the electrode interfaces. The blanking and recharge periods have short durations to avoid impinging on the negative deflection of the atrial evoked response 102 that peaks after about 20 ms, and thus, residual charge can remain at the electrodes. An example of this phenomenon is graphed as an electrode polarization 104, and shows that the current passing through the electrodes can cause an initial polarization of about −5 mV, after which the polarization exponentially decays with a time constant of about 100 ms. Accordingly, decay of the polarization on the electrodes can last longer than the atrial evoked response 102.

Referring to FIG. 2, a graph of an atrial evoked response waveform superimposed on an electrode polarization waveform is shown in accordance with an embodiment. The electrode polarization 104 challenges the detection of the atrial evoked response 102. The detection of cell depolarization (the atrial evoked response) occurs at the electrodes that have residual polarization. Accordingly, a detected signal 206 may include the residual charge on the cathode and the anode superimposed on the atrial evoked response 102. The electrode polarization 104, however, may be so large that the atrial evoked response 102 is obscured by the polarization potential. This is shown in FIG. 2, which illustrates the combined detected signal 206 as being on the same order of magnitude as the polarization potential. As a result, simple signal filtering may have difficulty selecting the atrial evoked response 102 out of the detected signal 206, which is dominated by the electrode polarization 104.

With the discoveries of FIGS. 1-2 as a backdrop, it will be understood that reduction of the residual polarization on the anode and/or the cathode may allow simple signal filtering, e.g., bandpass filtering or signal crossing, to be used to select the atrial evoked response 102 out of the detected signal 206. By reducing the electrode polarization 104, the detected signal 206 can be on the same order of magnitude as the atrial evoked response 102. Reduction of the electrode polarization 104 can be achieved by a biostimulator configured as described below.

Figure 3:
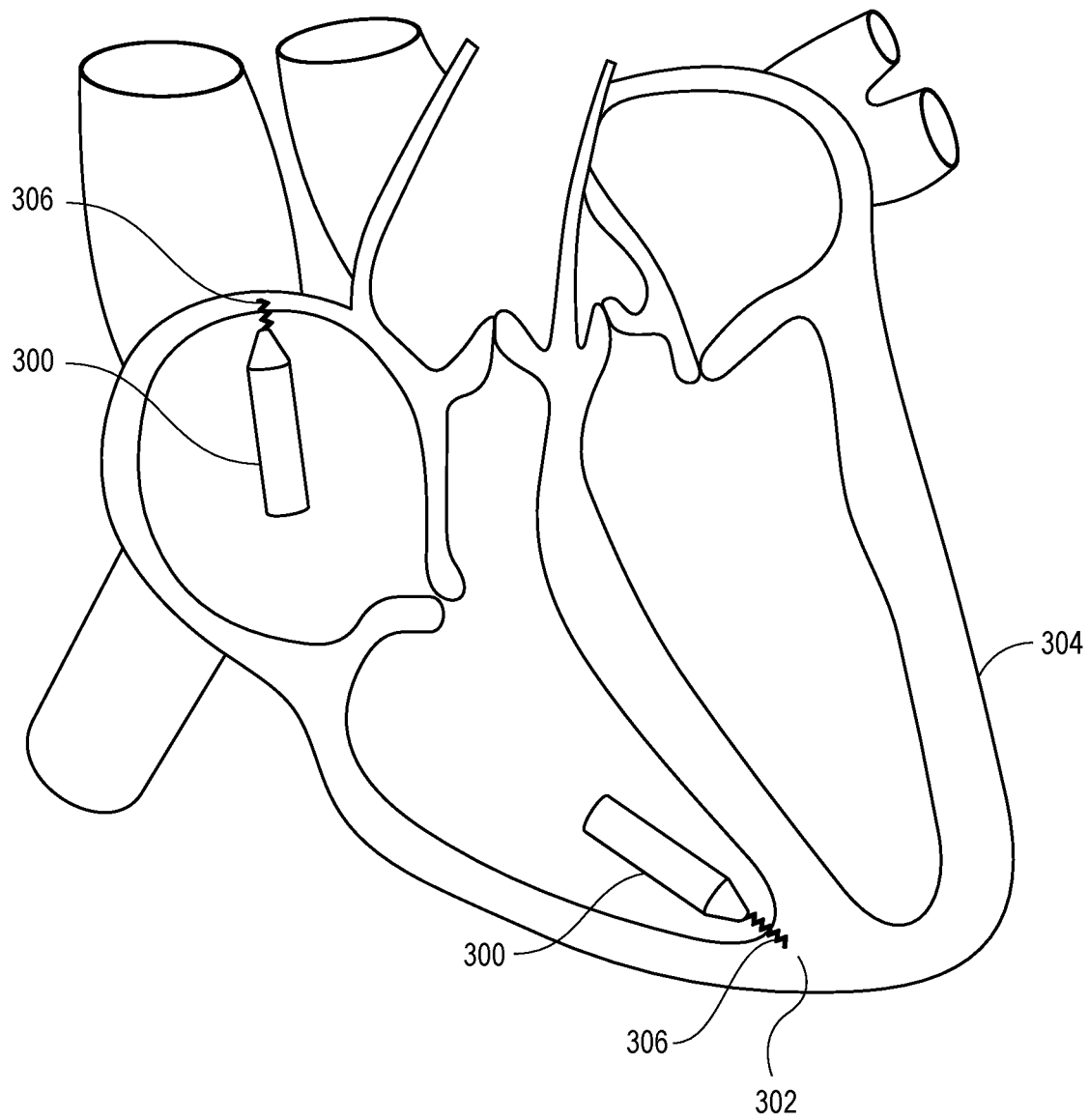
FIG. 3 is a diagrammatic medial-lateral cross section of a patient heart illustrating an example implantation of biostimulators in the patient heart, in accordance with an embodiment.

Referring to FIG. 3, a diagrammatic medial-lateral cross section of a patient heart illustrating an example implantation of biostimulators in the patient heart is shown in accordance with an embodiment. A cardiac pacing system includes one or more biostimulators 300. The biostimulator(s) 300 can be implanted at respective target sites in a patient. For example, the biostimulator(s) 300 can be implanted within a target tissue 302 in a heart 304 of the patient.

The biostimulator(s) 300 can be leadless biostimulators, such as leadless cardiac pacemakers. Each biostimulator 300 can be placed in a cardiac chamber, such as a right atrium and/or right ventricle of the patient heart 304, or attached to an inside or outside of the cardiac chamber. Attachment of the biostimulator 300 to the target tissue 302 can be accomplished via one or more fixation elements 306, such as helical anchors. In a particular embodiment, the leadless pacemaker can use two or more electrodes located on or within an enclosure or a body of the leadless pacemaker for pacing the cardiac chamber upon receiving a triggering signal from internal circuitry and/or from at least one other device within the body.

Referring to FIG. 4A a perspective view of a biostimulator delivery system is shown in accordance with an embodiment. A biostimulator system can include a biostimulator transport system 400 used for delivery and/or retrieval of the biostimulator 300, e.g., a leadless pacemaker, into or from a patient. For example, the biostimulator transport system 400 can be a biostimulator delivery system 402 used for delivery of the biostimulator 300 into a patient.

The biostimulator transport system 400 can include a handle 404, and an elongated catheter 406 extending distally from the handle 404 to a distal catheter end 408. The handle 404 can include several portions, e.g., a distal handle portion 410 and a proximal handle portion 412, and features that allow a user to provide inputs at a proximal end of the system that translate to outputs at the distal end of the system. For example, the elongated catheter 406 can be a deflectable catheter, and an operator can use the handle 404 to steer the distal catheter end 408 in the patient.

In an embodiment, the handle 404 includes a deflection lever 414 that can be used to deflect the distal catheter end 408. By pivoting the deflection lever 414 toward the distal handle portion 410 of the handle 404, the operator can cause a pull ring assembly extending within the elongated catheter 406 to apply off-axis compression to the elongated catheter 406, resulting in lateral deflection of the distal catheter end 408.

The handle 404 can be used to apply a torque to a docking cap 416 at the distal catheter end 408 of the system. In an embodiment, the proximal handle portion 412 can be rotationally and/or longitudinally moveable relative to the distal handle portion 410. For example, the distal handle portion 410 can be coupled to the elongated catheter 406 and the proximal handle portion 412 can be coupled to a torque shaft (not shown) extending within the elongated catheter 406. The docking cap 416 can be mounted on the torque shaft. Accordingly, an operator can rotate the proximal handle portion 412 relative to the distal handle portion 410 to impart torque to the torque shaft. The torque can cause the docking cap 416, which is rotationally linked to the proximal handle portion 412 through the torque shaft, to rotate relative to the elongated catheter 406, which is rotationally linked to the distal handle portion 410.

In an embodiment, the biostimulator transport system 400 includes a protective sheath 418 mounted on the elongated catheter 406. The protective sheath 418 can be slidably disposed on the elongated catheter 406. The protective sheath 418 can include an atraumatic end 420, e.g., a soft, funnel-shaped distal portion, that can slide distally over the distal catheter end 408 of the elongated catheter 406 and/or the biostimulator 300 (not shown). The atraumatic end 420 can have an outer dimension, which may be larger than a proximal portion of the protective sheath 418. For example, the atraumatic end 420 may flare in a distal direction to a funnel opening that can advance over a docking cap 416 of the biostimulator transport system 400. An outer dimension of the atraumatic end 420 can be larger than a region of the protective sheath 418 supporting a valve bypass tool 422.

The valve bypass tool 422 can be slidably disposed on the protective sheath 418 such that a distal portion of the valve bypass tool 422 can slide distally over the distal catheter end 408 of the elongated catheter 406 and/or the atraumatic end 420 of the protective sheath 418. More particularly, the valve bypass tool 422 can be inserted into an access introducer (not shown) to gain access to the patient vasculature, and after access is established, the distal portion of the protective sheath 418 and/or the distal end of the elongated catheter 406 can be advanced through the valve bypass tool 422 into the patient.

Referring to FIG. 4B, a distal perspective view of a biostimulator delivery system having a docking cap to receive a biostimulator is shown in accordance with an embodiment. The distal catheter end 408 of the elongated catheter 406 may be selectively connectable to the biostimulator 300. More particularly, the biostimulator 300 can be mounted on and/or coupled to the distal catheter end 408 of the elongated catheter 406. In an embodiment, the biostimulator 300 includes an attachment feature 450 that docks within or onto the docking cap 416. The attachment feature 450 can include a channel (not shown) shaped and sized to receive one or more tethers 452. The tethers 452 can comprise wires, shafts, tubes, cords, ropes, strings, or other similar structures that can extend throughout the catheter shaft. For example, the tethers 452 can extend through a shaft lumen of a torque shaft assembly. In some embodiments, the tethers 452 comprise a shape memory material, such as nickel-titanium. In other embodiments, the tethers 452 comprise stainless steel wires or braids. The tethers 452 can be inserted into and locked within the attachment feature 450 to connect the biostimulator 300 to the biostimulator transport system 400.

When the tethers 452 are locked within the attachment feature 450, the tethers can be retracted to pull the biostimulator 300 toward the docking cap 416. The docking cap 416 can include a docking cavity 454 having a shape and size to receive the attachment feature 450 of the biostimulator 300. As the biostimulator 300 moves toward the docking cap 416, the attachment feature 450 can insert into the docking cavity 454. Accordingly, the docking cavity 454 can receive the attachment feature 450 to dock the biostimulator 300 to the biostimulator delivery system 402 for delivery to the patient.

Torque can be transmitted from the docking cap 416 to the biostimulator 300 via the torque shaft when the attachment feature 450 is received in the docking cap 416. More particularly, the torque shaft can be rotated in a first direction, e.g., clockwise, to transmit torque through the docking cap 416 to the attachment feature 450, and to cause the fixation element 306 to engage and screw into the target tissue 302.

The biostimulator 300 can be protected by the atraumatic end 420 of the protective sheath 418 during delivery and/or retrieval of the biostimulator 300 from the patient. The atraumatic end 420 can have a braided or woven tubular construction. The atraumatic end 420 can therefore be advanced over the biostimulator 300 and may expand radially over the biostimulator in the case where an outer dimension of the biostimulator is greater than the inner diameter of the atraumatic end. Accordingly, the atraumatic end 420 can cover the biostimulator 300 to protect the biostimulator during advancement into the patient.

Figure 5A:
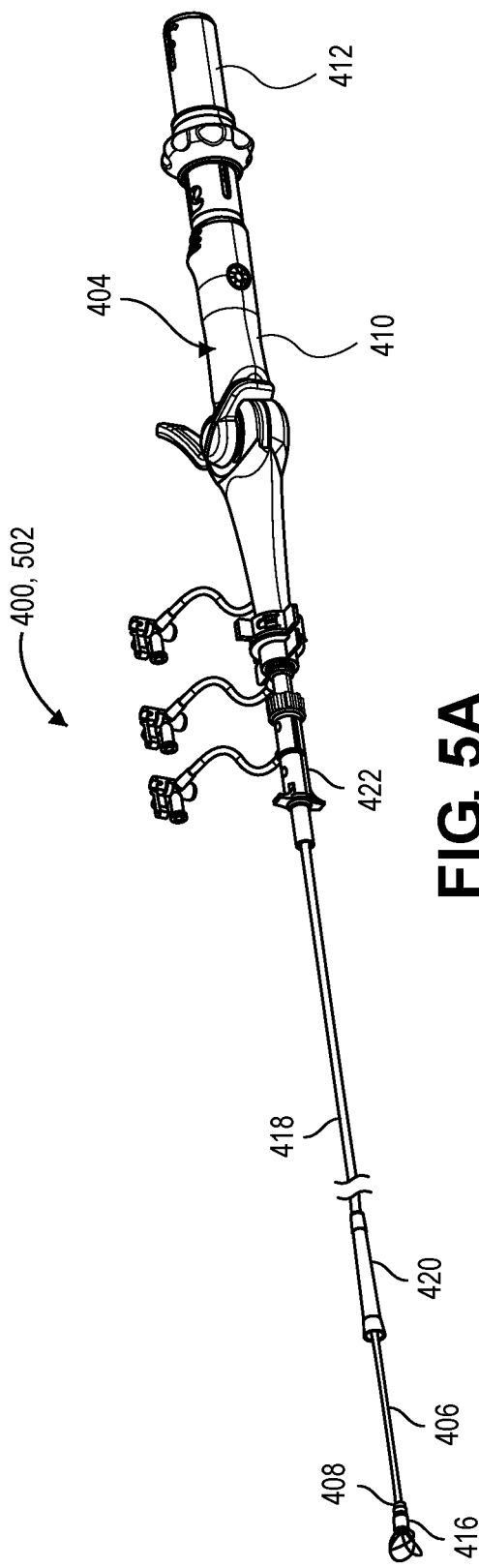
FIGS. 5A-5B are perspective views of a biostimulator retrieval system, in accordance with an embodiment.

Referring to FIG. 5A, a perspective view of a biostimulator retrieval system is shown in accordance with an embodiment. The biostimulator transport system 400 may be a biostimulator retrieval system 502. The biostimulator retrieval system 502 can be used to explant one or more biostimulator 300 from the atrium and/or the ventricle of the heart 304 of the patient. Removal and retrieval of the biostimulator(s) 300 may be accomplished endocardially. For example, the torque shaft of the elongated catheter 406 can be rotated in a second direction, e.g., counterclockwise, to disengage the biostimulator 300 from the target tissue 302. Accordingly, the biostimulator retrieval system 502 shown in FIG. 5A can have a structure similar to that shown and described with respect to the biostimulator delivery system 402 of FIG. 4A to retrieve the biostimulator 300 from a target anatomy. The similarly numbered components of the biostimulator retrieval system 502 are not described again here in the interest of brevity.

Figure 5B:
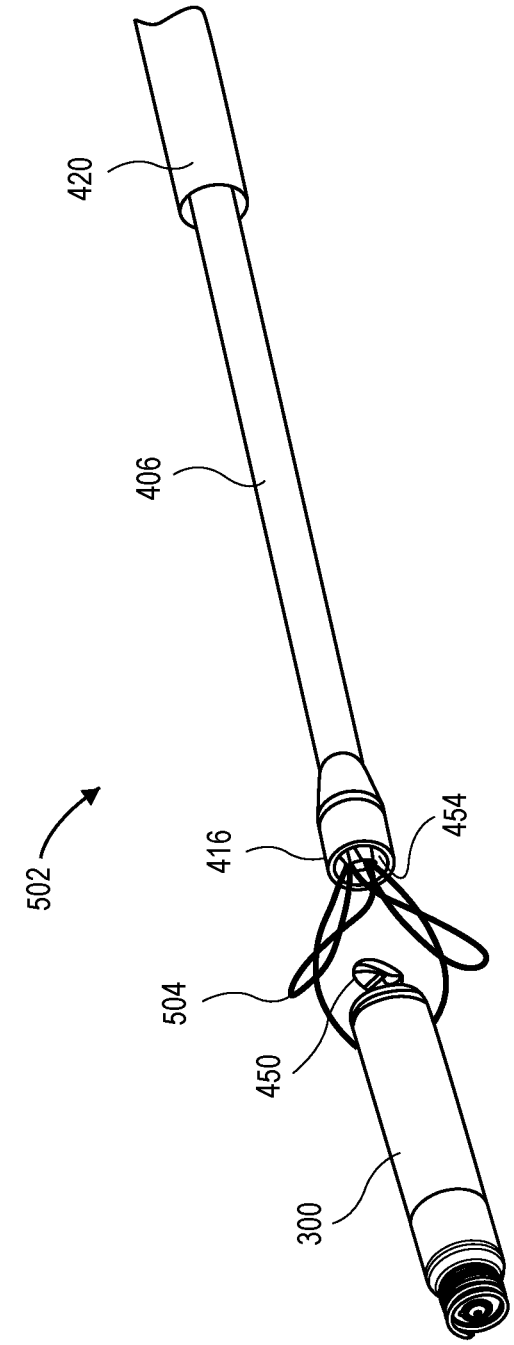

Referring to FIG. 5B, a perspective view of a biostimulator retrieval system is shown in accordance with an embodiment. The distal portion of the biostimulator retrieval system 502 can include features to engage the biostimulator 300 to facilitate capturing and unscrewing the biostimulator 300 from the target tissue 302. More particularly, the biostimulator retrieval system 502 can include a snare 504 extending through the elongated catheter 406 to grasp the biostimulator 300 or other medical device. The snare 504 can include at least one snare loop, e.g., a wire loop, extending from the elongated catheter 406. In some implementations, as in FIG. 5B, the snare 504 can include multiple loops, such as three loops. However, any number of loops can be used as long as the elongated catheter 406 contains sufficient volume to accommodate the loops.

As the snare 504 is advanced distally out of the biostimulator retrieval system 502 from the docking cap 416, the loop(s) can expand in size to aid a user in positioning the snare 504 around or in proximity to the biostimulator 300 to be retrieved. For example, the loop(s) can be positioned around or in proximity to the attachment feature 450.

The distal portion of the retrieval catheter can include the docking cap 416 configured to allow docking of the leadless pacemaker with the biostimulator retrieval system 502 after engaging the pacemaker with the snare 504. A user can transmit torque through the torque shaft via the handle 404 to rotate the docking cap 416 relative to the elongated catheter 406. More particularly, the torque shaft can extend through the length of the catheter to the handle 404, e.g., the proximal handle portion 412, which is coupled to the torque shaft. Rotation or actuation of the handle 404 rotates the torque shaft, thereby rotating the docking cap 416 at the end of the retrieval catheter. The protective sheath 418 can be positioned along the elongated catheter 406, and can be advanced or retracted to cover or expose the docking cap 416 and the leadless pacemaker using the atraumatic end 420.

During retrieval, the biostimulator retrieval system 502 can be navigated through the patient to the implant site. The snare 504 can be placed over the attachment feature 450 and the loops of the snare 504 can be reduced in size, thereby grasping or locking onto the attachment feature 450 of the pacemaker. Following capture and locking of the snare 504 with the leadless pacemaker, the biostimulator 300 may be docked within the docking cap 416. More particularly, the attachment feature 450 of the biostimulator 300 can be pulled into the docking cavity 454 of the docking cap 416. In some implementations, the docking cap 416 can include a key or interference feature configured to mate with and engage a corresponding key or feature on the biostimulator 300. In some implementations, the key or slot on the docking cap 416 can match a unique shape or feature of the attachment feature 450 of the pacemaker. Because the key or slot on or in the docking cap 416 can mate with and engage the attachment feature 450 of the pacemaker, the retrieval catheter can be configured to apply torque to the pacemaker to unscrew and remove the pacemaker from tissue.

Figure 6B:
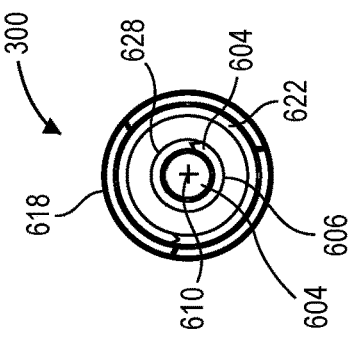
FIGS. 6A-6B are, respectively, side and end views of a biostimulator having low-polarization coating(s) on electrode(s), in accordance with an embodiment.
Figure 6A:
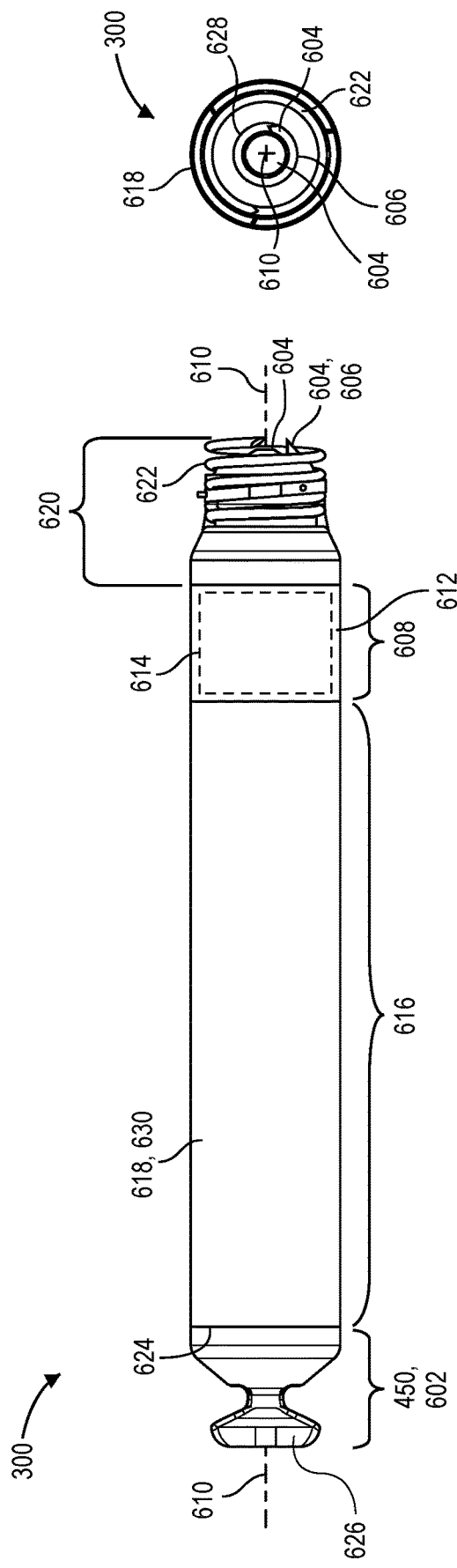

Referring to FIG. 6A, a side view of a biostimulator having low-polarization coating(s) on electrode(s) is shown in accordance with an embodiment. The biostimulator 300 can be a leadless pacemaker that can perform cardiac pacing and that has many of the advantages of conventional cardiac pacemakers while extending performance, functionality, and operating characteristics. The biostimulator 300 can have two or more electrodes, e.g., a proximal electrode or anode 602, and a distal electrode or cathode 604, located within, on, or near an enclosure or a body of the biostimulator 300. The distal electrode can be a dome-shaped electrode that is centrally located along the longitudinal axis 610. In an embodiment, one or more of the fixation elements 306 forms at least a portion of the distal electrode. For example, an inner fixation element 606 can act as an electrode, e.g., the cathode 604. In certain embodiments, the inner fixation element 606 is the only distal electrode. For example, the dome-shaped electrode may be omitted and/or may be a smooth distal surface of the biostimulator 300 that does not serve an electrical function. The electrodes can deliver pacing pulses to muscle of the cardiac chamber. Optionally, the electrode can sense electrical activity from the muscle. For example, the electrodes may be used to sense a chamber evoked response to implement autocapture.

In an embodiment, the enclosure or a body of the biostimulator 300 can include a housing 608. The housing 608 can have a longitudinal axis 610, and the distal electrode can be a distal pacing electrode mounted on or coupled to the housing 608 along the longitudinal axis 610. The housing 608 can include a housing wall 612 containing an electronics compartment 614 (shown by hidden lines) to hold circuitry adapted for different functionality. For example, the electronics compartment 614 can contain: circuits for sensing cardiac activity, such as the atrial evoked response 102, from the electrodes; circuits for receiving information from at least one other device via the electrodes; circuits for generating pacing pulses for delivery to tissue via the electrodes; or other circuitry. The electronics compartment 614 may contain circuits for transmitting information to at least one other device via the electrodes and can optionally contain circuits for monitoring device health. The circuitry of the biostimulator 300 can control these operations in a predetermined manner. In some implementations of a cardiac pacing system, cardiac pacing is provided without a pulse generator located in the pectoral region or abdomen, without an electrode-lead separate from the pulse generator, without a communication coil or antenna, and without an additional requirement of battery power for transmitted communication.

The enclosure or the body of the biostimulator 300 can include a battery assembly 616. The battery assembly 616 may be a primary battery to provide power for pacing, sensing, and communication, which may include, for example, bidirectional communication with at least one other device. In an embodiment, the battery assembly 616 includes a cell can 618. The cell can 618 may be coupled to the housing 608. For example, the housing 608 may be mounted on a distal end of the cell can 618. The cell can 618 contains an electrolyte and provides the power for pacing and sensing to the electronics within the electronic compartment 614 via feedthroughs. More particularly, the battery assembly 616 can include a separator, which may be a bag containing the electrolyte, and the separator can be contained within the cell can 618. In an embodiment, the cell can 618 is in direct contact with the separator. For example, the cell can 618 may include an annular wall having an outer surface facing a surrounding environment and an inner surface in contact with the separator.

The annular wall of the cell can 618 extends along the longitudinal axis 610. More particularly, the annular wall can extend longitudinally from a distal battery end to a proximal battery end. The battery assembly 616 can include positive and negative terminals at the distal end (not shown). The terminals can be electrically coupled to the electrolyte to transfer power from the battery assembly 616 to the internal electronics within the electronics compartment 614.

Leadless pacemakers or other leadless biostimulators can be fixed to an intracardial implant site by one or more actively engaging mechanism or fixation mechanism, such as a screw or helical member that screws into the myocardium. In an embodiment, the biostimulator 300 includes several fixation elements 306 coupled to the housing 608. More particularly, the biostimulator 300 can include a header assembly 620 mounted on a distal end of the housing 608. An outer fixation element 622 can be mounted on the header assembly 620, and thus, coupled to the housing 608.

The outer fixation element 622 can be a helical element to screw into target tissue 302. More particularly, the outer fixation element 622 can extend helically from a flange of the biostimulator 300, which is mounted on the housing 608, to a distal end at a distal tip of the helix. Accordingly, the outer fixation element 622 can include an outer helix. Similarly, the inner fixation element 606 can be coupled to the housing 608 by the header assembly 620. More particularly, the inner fixation element 606 can extend helically from the flange to a distal end at a distal tip of the helix. Accordingly, the inner fixation element 606 can include an inner helix. In an embodiment, the inner helix and the outer helix revolve about the longitudinal axis 610. The inner fixation element 606 can be coaxially arranged with the outer fixation element 622 (FIG. 6B). More particularly, the inner helix can be radially inward of the outer helix, e.g., radially between the outer helix and the longitudinal axis 610. When the biostimulator 300 contacts the target tissue 302, the distal tips of the inner fixation element 606 and the outer fixation element 622 can pierce the tissue and the housing 608 can be rotated to screw the outer fixation element 622 into the target tissue 302 to pull the distal electrode 604 into contact with the tissue.

The biostimulator 300 can include the attachment feature 450 coupled to the battery assembly 616. More particularly, the attachment feature 450 may be mounted on and/or attached to a proximal end of the cell can 618. In an embodiment, the attachment feature 450 is coupled to the battery assembly 616 by a weld 624, e.g., a laser weld. For example, the weld 624 can extend circumferentially around the cell can 618 and a proximal lip of the attachment feature 450, as described below. As described above, the attachment feature 450 may be captured by tethers 452 or a snare 504 of the biostimulator transport system 400 and used to transmit torque from the docking cap 416 to the enclosure or body of the biostimulator 300. Accordingly, the attachment feature 450 allows torque to be transmitted to the fixation elements 306 to screw the biostimulator 300 into the target tissue 302. Both the fixation elements 306, e.g., the inner fixation element 606, and the attachment feature 450, however, can also provide electrical function. More particularly, the attachment feature 450 may be the anode 602 of the biostimulator 300, and the inner fixation element 606 may be the cathode 604 of the biostimulator 300.

To facilitate electrical function of the anode 602, e.g., the attachment feature 450, and the cathode 604, e.g., the inner fixation element 606, the elements may be coated in respective low-polarization coatings. Such coatings can reduce polarization of the electrodes by rendering the surface area of the electrodes effectively larger, and thus, increasing the overall capacitance of the surfaces (which in turn reduces the polarization of the surfaces).

An example can help illustrate the substantial impact that low-polarization coatings on an exterior surface 626 of the attachment feature 450 and/or an outer surface 628 of the inner fixation element 606 can have on the polarization of the elements. It has been found that, for the attachment feature 450 having the structure described below and formed from titanium, a polarization of 800 mV may develop on the anode surface under a standard test (described below). Such a polarization will obscure the atrial evoked response 102 (FIG. 2). When treated with the low-polarization coating described below, however, a polarization of only 10 mV develops on the anode surface. Likewise, it has been found that for the inner fixation element 606 having the structure described below and formed from platinum iridium, a polarization of 1000 mV may develop on the cathode surface under the standard test. Such a polarization will obscure the atrial evoked response 102. When treated with the low-polarization coating described below, however, a polarization of only 10-20 mV develops on the cathode surface. These examples represent substantial reductions in the electrode polarization 104 that can allow the biostimulator 300 to detect the atrial evoked response 102 using simple signal processing techniques.

By way of reference, the standard test referred to above includes a 1 ms duration, 10 milliamp constant current pulse applied in 0.9% sodium chloride solution between the electrode (e.g., the inner fixation element 606 or the attachment feature 450) and a large area titanium nitride plate. During the pulse, the voltage potential between the electrodes increases as the polarization builds up a capacitive double layer. The polarization voltage potential is a measure of the polarizability of the electrodes, and can be measured by an electronic system from a beginning to an end of the constant current pulse to determine the electrode polarization 104.

In an embodiment, the biostimulator 300 includes an insulating coating 630 on the cell can 618. The insulating coating 630 may be a parylene coating, for example. The insulating coating 630 can provide insulation from the surrounding tissue to limit or prevent the flow of electrical current through the cell can 618 and direct the electrical current to go through the attachment feature 450 instead. Accordingly, an entire outer surface of the cell can 618 may be coated by the insulating coating 630, e.g., from the weld 624, which attaches the attachment feature 450 to the cell can 618, to a weld that attaches the cell can 618 to the housing 608. Similarly, an outer surface of the housing 608 and/or the flange of the header assembly 620 may be coated by the insulating coating 630. Accordingly, in an embodiment, electrical current may only flow through the inner fixation element 606 and the attachment feature 450. By separating the anode 602 and the cathode 604 as far as possible, e.g., by creating an insulator intermediate between the electrodes using the insulating coating 630, the chamber evoked response may become wider. A wider evoked response may be easier to detect because less bandwidth is required to detect such a response. Accordingly, the insulating coating 630 on the cell can 618, when combined with low-polarization coated electrodes as described herein, may promote detection of the chamber evoked response using simple signal processing techniques.

For completeness, it is noted that the battery assembly 616 may also be coated with a non-polarizable coating. That is, the low-polarization coating used on either the attachment feature 450 or the inner fixation element 606 may also be applied to the outer surface of the cell can 618. Such a coating can increase anode surface area and thereby decrease anode 602 polarization at the cost of less spacing between the electrodes.

In an embodiment, the low-polarization coating on the exterior surface 626 of the attachment feature 450 includes one or more non-polarizing materials. For example, the low-polarization coating on the attachment feature 450 may include one or more of titanium nitride, iridium oxide, or platinum black. The exterior surface 626 can be an outward facing surface of the attachment feature 450, which may be fabricated from titanium, for example.

In an embodiment, the low-polarization coating on the outer surface 628 of the inner fixation element 606 is a dual-layer coating. More particularly, the dual-layer coating can include a first layer, or a base layer, coated on the outer surface 628 of the inner fixation element 606. A second layer may then be coated on the first layer. In an embodiment, the first layer includes titanium nitride sputtered on the outer surface 628 of the inner fixation element 606. The second layer can include platinum black. More particularly, the second layer can be an electrode-deposited layer of platinized platinum covering the first layer and the outer surface 628 of the inner fixation element 606. Thus, the first layer may be between the second layer and the outer surface 628 of the inner fixation element 606.

The advantage of applying the dual-layer coating to the inner fixation element 606 has been proven through testing. Using the standard test, applying a single titanium nitride coating to the inner fixation element 606 provided a polarization of 73 mV. By contrast, when the standard test was used on the inner fixation element 606 having the dual-layer coating including the first layer of titanium nitride and the second layer of platinum black, the polarization reduced to 41 mV. Additional platinization reduced the polarization even further. For example, platinization for 30 minutes at 800 microamperes produced the 41 mV electrode polarization 104, whereas platinization for 1 hour at 800 microamperes produced an 18 mV electrode polarization 104.

The low-polarization coatings on the anode 602 and cathode 604 can render the electrode surface areas effectively larger. In the case of the anode 602, the geometrical surface area, not accounting for surface morphology, of the exterior surface 626 of the attachment feature 450 described below can be at least 150 mm$^2$, e.g., 177 mm$^2$. In the case of the cathode 604, the geometrical surface area of the outer surface 628 of the inner fixation element 606 geometry described below can be less than 20 mm$^2$, e.g., 8 mm$^2$. Thus, it may be necessary to effectively enlarge the surface area of the cathode 604 by more than the anode 602 to achieve a sufficient reduction in polarization of both electrodes. Effectively enlarging the surface area can be achieved by increasing the surface area, accounting for surface morphology.

In an embodiment, the low-polarization coating on the anode 602 includes a morphology having a microstructure on the order of 500 nm. It is contemplated that the dual-layer coating on the cathode 604 can include a morphology having a smaller microstructure than the microstructure on the anode 602, e.g., a smaller microstructure than 500 nm. The smaller microstructure can provide a larger effective surface area, accounting for the morphology, per geometrical surface area, not accounting for the morphology, than a larger microstructure can. The effective surface area can take into account the morphology, e.g., surface roughness, as compared to the geometrical surface area, which does not. Thus, although the inner fixation element 606 can have a smaller geometrical surface area than the attachment feature 450, a ratio of the geometrical surface area of the inner fixation element 606 to the geometrical surface area of the attachment feature 450 can be smaller than a ratio of the effective surface area of the inner fixation element 606 to the effective surface area of the attachment feature 450. The platinization process of electrode depositing platinum creates further submicron surface structure on the inner fixation element 606 that achieves the necessary true surface area to reduce the electrode polarization 104.

Figure 7:
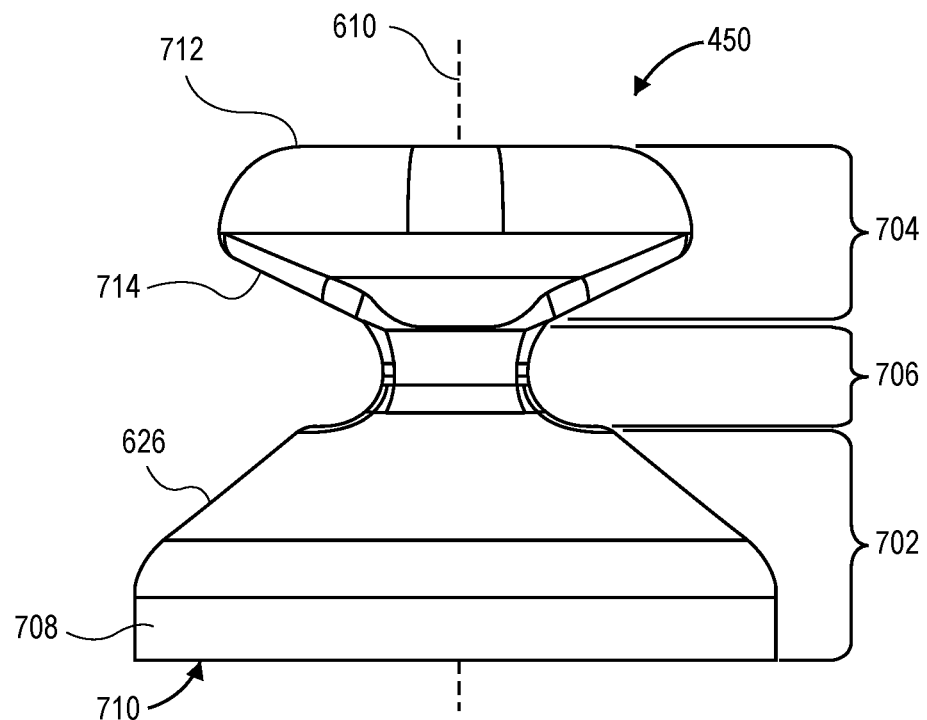
FIGS. 7-8 are side elevation views of an attachment feature, in accordance with an embodiment.
Figure 8:
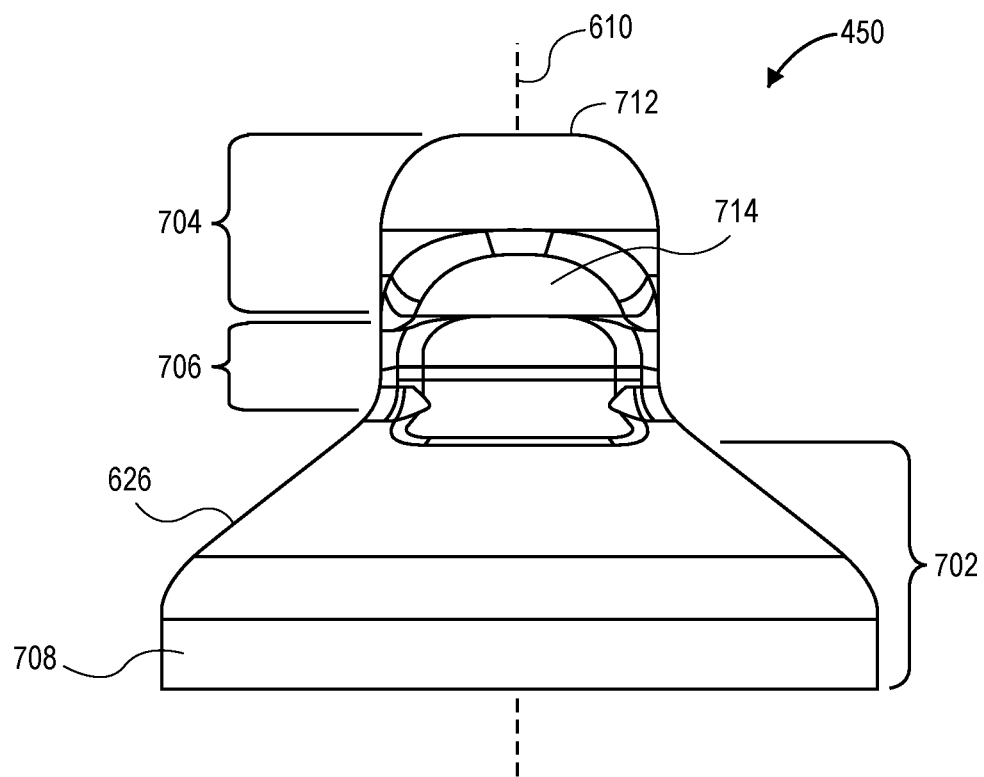

Referring to FIGS. 7-8, side elevation views of an attachment feature 450 are shown. In an embodiment, the attachment feature 450 can include a base 702, a button 704, and a stem 706. The attachment feature 450 can have a one-piece construction. For example, the attachment feature 450 can be monolithically formed from a rigid material, e.g., titanium, such that the base 702, the button 704, and the stem 706 are all portions of a single structure. The structure can have the stem 706 that includes a single post interconnecting the base 702 to the button 704 such that the monolithic attachment feature 450 is strong and stiff. The rigid attachment feature 450 can therefore transmit torque efficiently from a delivery or retrieval system to the leadless pacemaker.

In an embodiment, the base 702 includes a distal flange 708. The distal flange 708 can be a tubular section of the attachment feature 450. For example, the distal flange 708 can have a cylindrical outer surface and may include a flange port 710 within the outer surface. The flange port 710 can surround the longitudinal axis 610 that extends in the longitudinal direction through the attachment feature 450. For example, the distal flange 708 can have an inner surface extending around the longitudinal axis 610, which defines the flange port 710.

The button 704 can be disposed along the longitudinal axis 610. For example, the button 704 can have a proximal button face 712 that extends orthogonal to the longitudinal axis 610. In an embodiment, the proximal button face 712 has a face port (FIGS. 9-10) surrounding the longitudinal axis 610. For example, the button 704 can have an inner surface extending around the longitudinal axis 610, which defines the face port.

The stem 706 can be disposed along the longitudinal axis 610 between the base 702 and the button 704. In an embodiment, the stem 706 has an annular stem wall (FIG. 10) that extends from a distal end at the base 702 to a proximal end at the button 704. The stem portion may be continuous with the base 702 and button portions of the attachment feature 450. Transitions between the portions can be made in various manners. The stem 706 may have a smaller transverse dimension than both the base 702 and the button 704 in at least one side view. For example, the transverse dimension of the stem 706 in the side view of FIG. 7 may be a minimum transverse dimension of the attachment feature 450. By contrast, the transverse dimension of the button 704 and the stem 706 may be equal and minimum transverse dimensions of the attachment feature 450 in the side view of FIG. 8.

One or more of the base portion or the button portion of the attachment feature 450 can transition smoothly into the stem 706. For example, the base 702 can include a tapered body that tapers radially inward from the distal flange 708 toward the stem 706. In an embodiment, the distal flange 708 has a circular transverse profile taken about a plane extending through the flange orthogonal to the longitudinal axis 610, and the stem 706 has a rectangular transverse profile. A diameter of the circular transverse profile can be greater than a length of a side of the rectangular transverse profile. Accordingly, the base 702 can have a smaller and smaller circular transverse profile diameter at each point between the distal flange 708 and an outer proximal end of the base 702.

The exterior surface 626 of the attachment feature 450 can transition abruptly inward along a transverse face at the outer proximal end from the tapered body to the stem 706 in at least one side view (FIG. 7). By contrast, the tapered body may transition gradually into stem 706 (no discontinuity) at the outer proximal end in another side view (FIG. 8).

In an embodiment, the distal button face 714 tapers radially inward from the proximal surface of the button 704 toward the stem 706. For example, the distal button face 714 can include an angled plane that extends from a transverse perimeter of the button 704 toward the stem 706. The distal button face 714 that extends along the angled plane, which is oblique to the longitudinal axis 610, can transition from the transverse perimeter toward the stem 706. The transverse perimeter can be a profile taken along a transverse plane passing through the button 704 orthogonal to the longitudinal axis 610. In an embodiment, the transverse perimeter is taken at an outwardmost point along the outer surface of the button 704. Accordingly, the transverse perimeter can represent a largest perimeter of any transverse cross-section taken through the button 704.

In an embodiment, a transverse profile of the stem 706 extends around the longitudinal axis 610. For example, the stem 706 can be a single elongated rectangular post having a rectangular cross-section that is lofted along the longitudinal axis 610. Alternatively, the stem 706 can be a single elongated cylindrical post having a circular cross-section that extends along the longitudinal axis 610. Similar unitary post structures can have triangular, elliptical, etc., transverse profiles. The transverse profile of the stem 706 may be defined in part by a major stem axis and a minor stem axis, which may have equal (in the case of a square cross-section) or different (in the case of a rectangular cross-section) dimensions.

Figure 9:
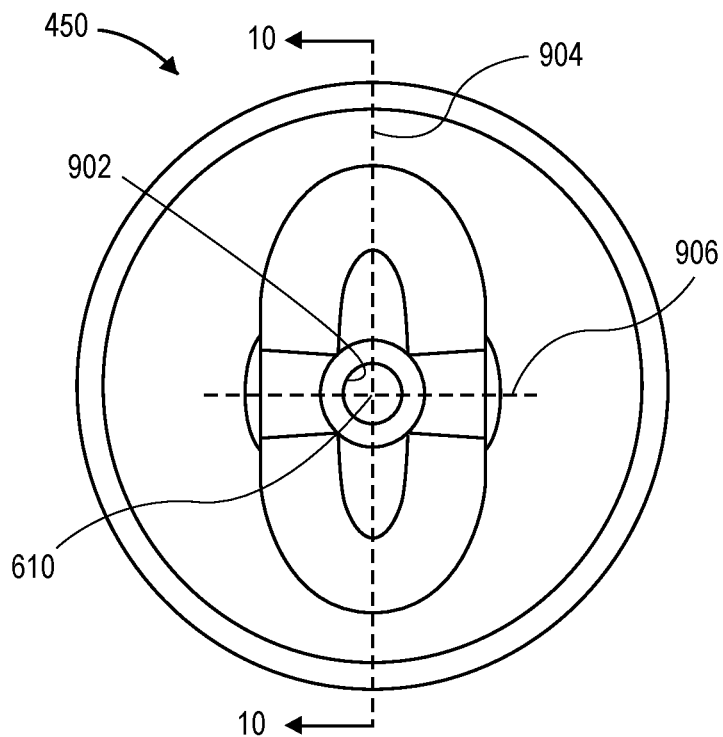
FIG. 9 is a proximal view of the attachment feature of FIGS. 7-8, in accordance with an embodiment.

Referring to FIG. 9, a proximal view of the attachment feature of FIGS. 7-8 is shown. The transverse perimeter of the button 704 can have an oval shape. For example, the transverse perimeter can have a major axis 904 and a minor axis 906 that differ to define the oval shape. The oval shape may be symmetric about one or more of the major axis 904 and the minor axis 906. For example, as shown in FIG. 9, the oval shape can be an ellipse, which is symmetric about both axes. The transverse perimeter could be egg-shaped, and thus, may be symmetric about only one of the axes. The ellipse may have a curved segment with a curve length, and the curved segment can be a portion of the ellipse that intersects the major axis 904. In an embodiment, the ellipse has a straight segment having a straight length, and the straight segment intersects the minor axis 906. In other embodiments, the portion of the oval shape intersecting the major axis 904 can be straight and the portion intersecting the minor axis 906 can be curved.

Figure 10:
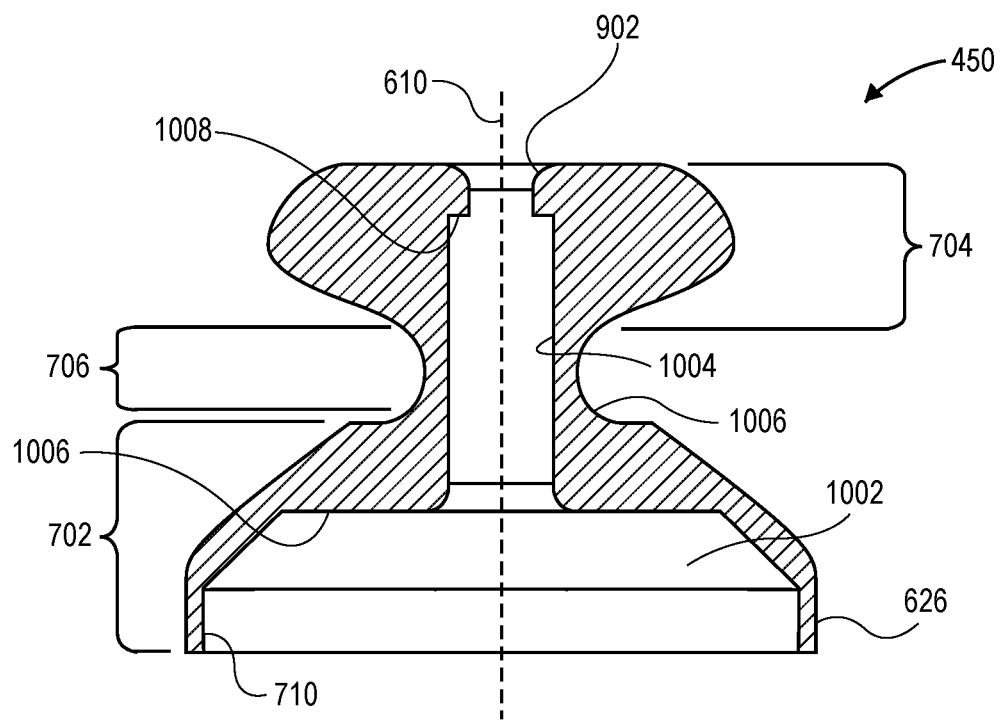
FIG. 10 is a cross-sectional view of the attachment feature of FIGS. 7-8, taken about section line 10-10 of FIG. 9, in accordance with an embodiment.

Referring to FIG. 10, a cross-sectional view of the attachment feature of FIGS. 7-8, taken about section line 10-10 of FIG. 9, is shown. In an embodiment, the attachment feature 450 includes an internal cavity 1002 that is laterally surrounded by the base 702, the button 704, and the stem 706. For example, the internal cavity 1002 can extend along the longitudinal axis 610 from the face port 902 to the flange port 710. The internal cavity 1002 can extend through the base 702, the button 704, and the stem 706 in the longitudinal direction from the proximal end of the attachment feature 450 to the distal end. Accordingly, the internal cavity 1002, provides an opening to receive tethers 452 of a delivery or retrieval system for docking and undocking, as described above.

The internal cavity 1002 extending longitudinally through the stem 706 can produce an annular transverse profile. Rather than being a solid post, the stem 706 can have a tubular structure. The tubular stem 706 can have an outer surface, provided by the exterior surface 626 of the attachment feature 450. An interior surface 1004 of the attachment feature 450 can extend around the internal cavity 1002 and can be an inner surface of the tubular stem 706. More particularly, the exterior surface 626 and the interior surface 1004 can be continuous and define an annular stem wall 1006 surrounding the longitudinal axis 610. Accordingly, the stem 706 can have an inner lumen that extends longitudinally between the base 702 and the button 704.

The internal cavity 1002 that extends longitudinally through the attachment feature 450 and is surrounded in the transverse direction by an inner surface of the attachment feature 450 can be further defined in terms of cavity portions. For example, a mounting cavity of the internal cavity 1002 can extend from the distal end of the distal flange 708 to an inner proximal face 1006 of the base 702. The mounting cavity may be a region of the internal cavity 1002 that receives a portion of a cell can 618, e.g., an end boss of the cell can 618, as described below. The inner proximal face 1006 can extend orthogonal to the longitudinal axis 610. The inner surface of the attachment feature 450 surrounding the mounting cavity can have a similar form to the exterior surface 626 of the attachment feature 450 surrounding the inner surface. For example, a region of the mounting cavity within the distal flange 708 can be cylindrical, and a region of the mounting cavity within the tapered body can be frustoconical.

The internal cavity 1002 can include a tethering cavity proximal to the mounting cavity. The tethering cavity may be a region of the internal cavity 1002 that receives tethers 452 of a delivery or retrieval system during docking or undocking of a leadless pacemaker, as described above. More particularly, the tethering cavity can have a width greater than a combined width of two tether distal features. The tethering cavity can extend proximally from the inner proximal face 1006 of the base 702 to an inner distal face 1008 of the button 704. The inner distal face 1008 can extend orthogonal to the longitudinal axis 610. The inner surface of the attachment feature 450 surrounding the tethering cavity (part of which is interior surface 1004) can be cylindrical.

The internal cavity 1002 can include a passage cavity proximal to the tethering cavity. The passage cavity may be a region of the internal cavity 1002 that receives tethers 452 of a delivery or retrieval system during docking or undocking of a leadless pacemaker, as described above. More particularly, the passage cavity can have a width less than a combined width of two tether distal features. The passage cavity can extend proximally from the inner distal face 1008 to the face port 902. The inner surface of the attachment feature 450 surrounding the passage cavity may, for example, be cylindrical.

All or a portion of the surfaces of the attachment feature 450 described above can be coated by the low-polarization coating. In an embodiment, the low-polarization coating covers an entirety of the exterior surface 626. The exterior surface 626 includes those surfaces visible in FIGS. 7-9. By contrast, the low-polarization coating may cover only a portion of the interior surface 1004. For example, only portions of the interior surface 1004 susceptible to overspray during the titanium nitride sputtering process may be coated. Such portions may include the region of the interior surface 1004 near the proximal end, e.g., near the face port 902, and the distal end, e.g., near the flange port 710, of the internal cavity 1002. The low-polarization coating can therefore reduce polarization of the attachment feature 450 by increasing the true surface area of only the exterior surface 626.

Figure 11:
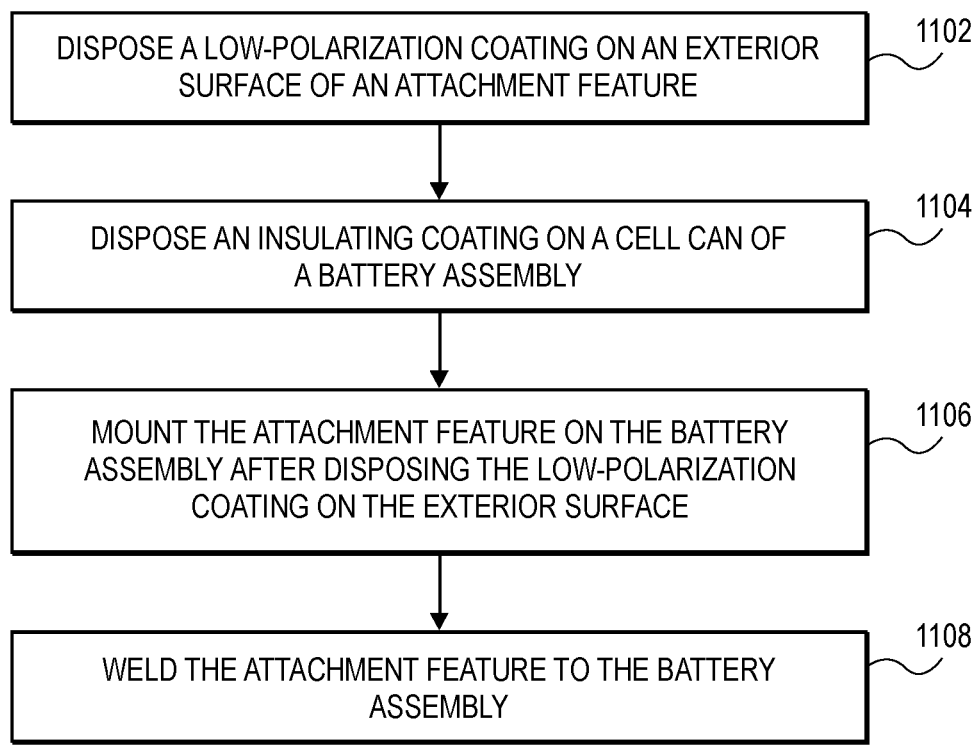
FIG. 11 is a flowchart of a method of fabricating a biostimulator having a low-polarization coating on an attachment feature, in accordance with an embodiment.

Referring to FIG. 11, a flowchart of a method of fabricating a biostimulator having a low-polarization coating on an attachment feature is shown in accordance with an embodiment. The biostimulator 300 may have the low-polarization coating on the attachment feature 450, and may or may not have a low-polarization coating on the inner fixation element 606. The process of manufacturing the biostimulator 300 to include the coated attachment feature 450 coupled to the battery assembly 616 may begin at operation 1102, in which the low-polarization coating is disposed on the exterior surface 626 of the attachment feature 450. Disposing the low-polarization coating on the attachment feature 450 can include sputtering one or more of titanium nitride or iridium oxide onto the exterior surface 626. The low-polarization coating can cover an entirety of the exterior surface 626 and all or some of the interior surface 1004 of the attachment feature 450. The sputtering process may be performed when the attachment feature 450 is not yet coupled to the battery assembly 616. More particularly, the attachment feature 450 can be coated with the low-polarization coating prior to assembling the biostimulator 300.

At operation 1104, the insulating coating 630 may optionally be disposed on the cell can 618 of the battery assembly 616. The insulating coating 630 may extend over the annular wall of the cell can 618 from the distal battery end to the proximal battery end. Like the coating of the attachment feature 450, the insulation of the cell can 618 may be applied when the battery assembly 616 is at the subcomponent level. More particularly, the cell can 618 may be insulated prior to assembling the biostimulator 300.

At operation 1106, the attachment feature 450 is mounted on the battery assembly 616. The mounting of the distal flange 708 of the attachment feature 450 on to the proximal battery end can occur after disposing the low-polarization coating on the exterior surface 626 of the attachment feature 450. Doing so provides for a convenient and robust manufacturing process, because it has been found that covering the attachment feature 450 with the low-polarization coating after the attachment feature 450 is coupled to the battery assembly 616 is more difficult.

At operation 1108, the attachment feature 450 is welded to the battery assembly 616 to secure the components to each other. More particularly, the attachment feature 450 may be welded to the battery assembly 616 circumferentially around the base 702 and the cell can 618. Laser welding may be used to form the weld 624 around the proximal battery end of the cell can 618 and the distal flange 708 of the attachment feature 450. The circumferential weld can be narrow, and thus, can have minimal impact on the integrity of the insulating coating 630 and the low-polarization coating. Accordingly, the biostimulator 300 having the anode 602 exhibiting low electrode polarization 104 can be provided.

Figure 12:
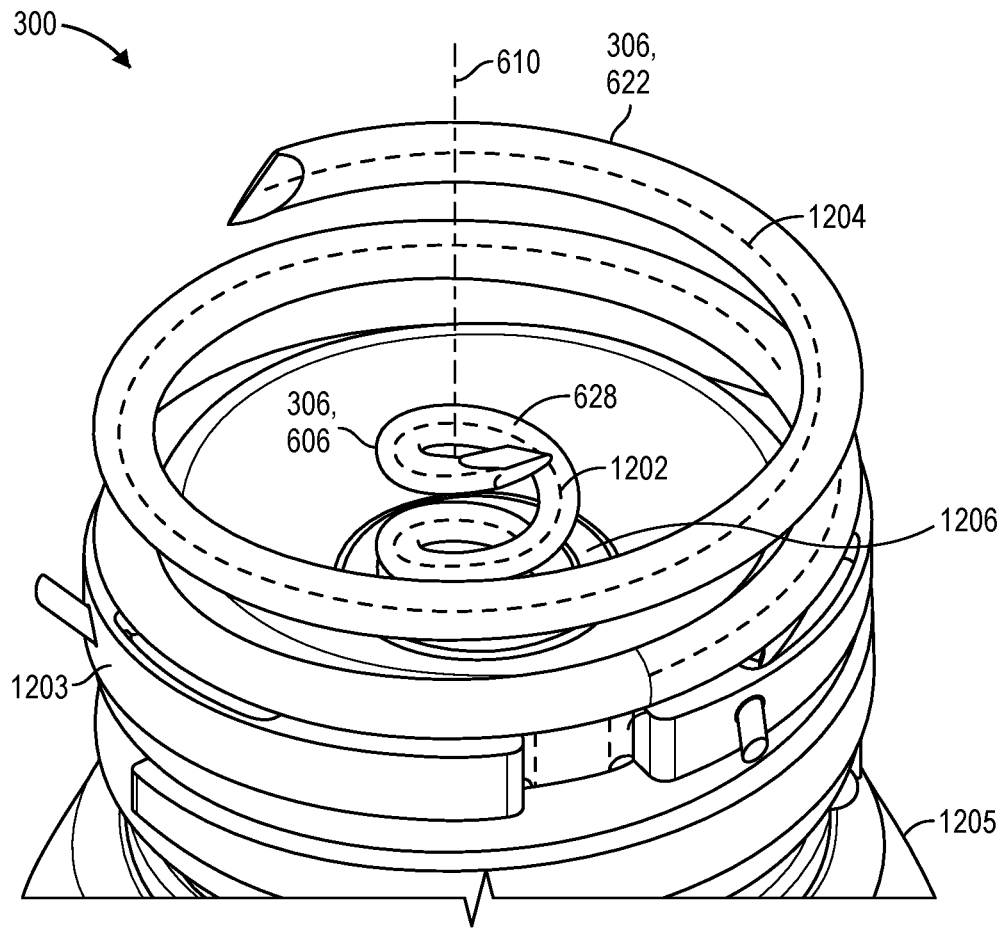
FIG. 12 is a perspective view of a distal portion of a biostimulator having coaxial fixation elements, in accordance with an embodiment.

Referring to FIG. 12, a perspective view of a distal portion of a biostimulator having coaxial fixation elements is shown in accordance with an embodiment. The biostimulator 300 can include the inner fixation element 606 nestled within the outer fixation element 622. More particularly, the inner fixation element 606 can include an inner helix 1202 that is radially inward from an outer helix 1204 of the outer fixation element 622. The helices can both extend or revolve about the longitudinal axis 610, and the fixation elements 306 can extend along the respective helices. A helix radius of the outer fixation element 622 may be greater than the helix radius of inner fixation element 606. As described below, the helices can have relative configurations that contribute to tissue piercing.

In an embodiment, the helices have a same clocking relative to the longitudinal axis 610. More particularly, the inner helix 1202 and the outer helix 1204 can revolve about the longitudinal axis 610 in a same direction. For example, both helices of the fixation elements 306 may extend about the longitudinal axis 610 in a counterclockwise, e.g., a right-handed, direction to the respective distal tips. Similar clocking of the helices can cause the fixation elements 306 to simultaneously advance or retract from the target tissue 302 when the biostimulator 300 is rotated. Alternatively, the helices may revolve about the longitudinal axis 610 in different directions.

The relative orientation characteristics of the fixation elements 306 can be predetermined. For example, the distal tips of the fixation elements 306 may terminate at different radial directions from the longitudinal axis 610, and an angular separation between the termination points can be controlled. It is contemplated that a greater angular distance between the distal tips of the fixation elements 306 can contribute to the fixation elements gaining greater purchase in the target tissue 302. The maximized separation can make it easier to torque the fixation elements 306 into the tissue, and as the fixation elements 306 screw into the tissue there is less chance that tunnels formed by the advancing fixation elements 306 will intersect within the tissue. Accordingly, a distance and an angular separation between the distal tips can be maximized to enhance tissue engagement.

The header assembly 620 of the biostimulator 300 can include a helix mount 1203, which can be mounted on the housing 608. For example, the helix mount 1203 can have an internal thread that mounts on an external thread of a flange 1205 by a threaded connection. The biostimulator 300 can include a cup 1206. In an embodiment, the inner fixation element 606 is mounted on the cup 1206 radially inward from the outer fixation element 622, which is mounted on the helix mount 1203. Pacing pulses can be transmitted through the cup 1206 to the inner fixation element 606 to pace the target tissue 302.

The cup 1206 may contain a filler (not shown). The filler can be referred to as a monolithic controlled release device (MCRD), and can include a therapeutic material. The therapeutic agent can include a corticosteroid, such as dexamethasone sodium phosphate, dexamethasone acetate, etc. Furthermore, the therapeutic agent can be loaded in a silicone matrix. Accordingly, the filler can deliver a specified dose of a therapeutic agent, e.g., a corticosteroid, into the target tissue 302. When the target tissue 302 is drawn in by the coaxial fixation elements 306 toward the cup 1206, as the biostimulator 300 is screwed into the tissue, the therapeutic agent can be effectively delivered into the tissue after the biostimulator 300 is implanted in a patient. Accordingly, inflammation or injury of the captured tissue may be reduced.

All or a portion of the surfaces of the inner fixation element 606 described above can be coated by the low-polarization coating. In an embodiment, the low-polarization coating covers an entirety of the outer surface 628 of the inner fixation element 606. The outer surface 628 includes the surfaces of the inner fixation element 606 visible in FIG. 12. As described above, the low-polarization coating on the outer surface 628 can include a dual-layer coating having a titanium nitride base layer covered by a platinized top layer. The low-polarization coating can therefore reduce polarization of the inner fixation element 606 by increasing the true surface area of the outer surface 628.

Figure 13:
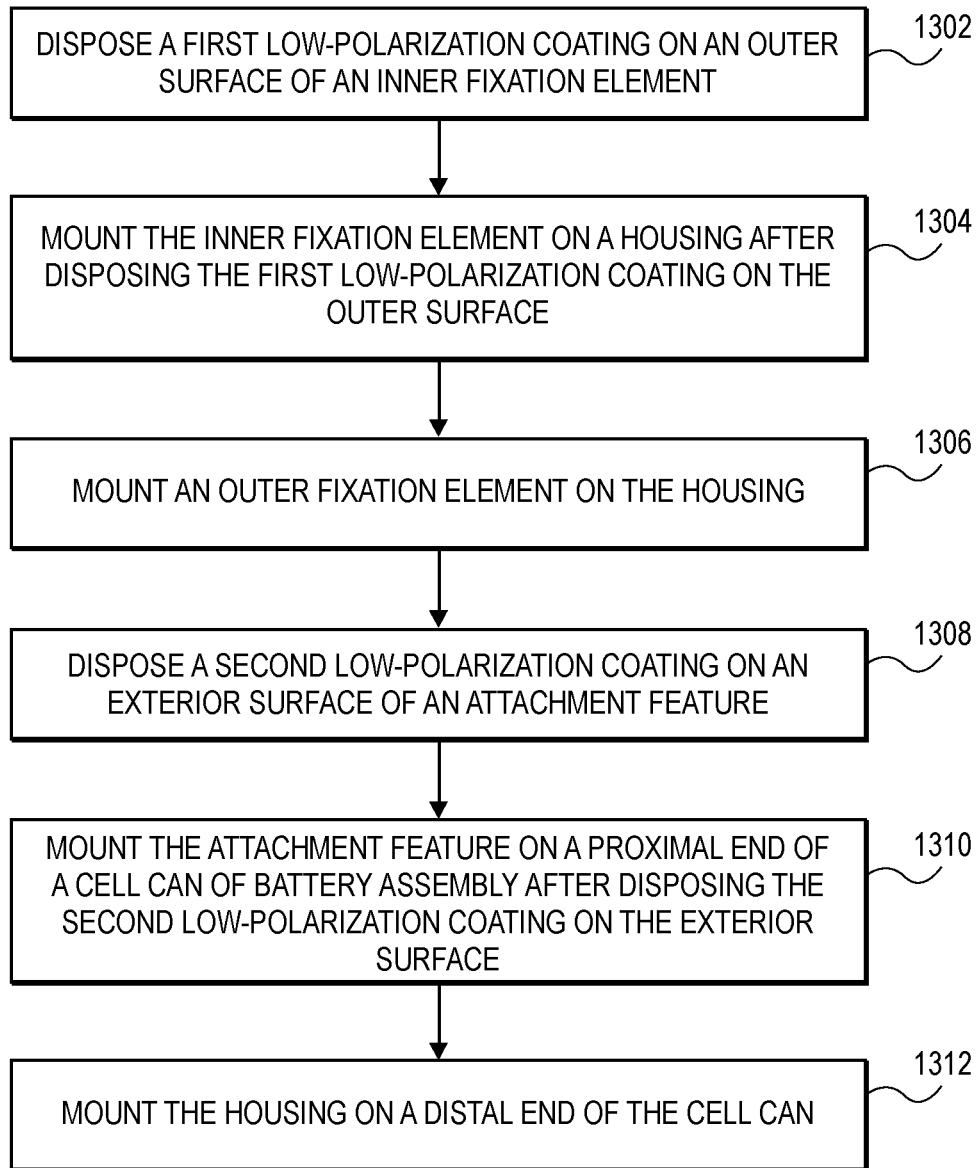
FIG. 13 is a flowchart of a method of fabricating a biostimulator having low-polarization coatings on an inner fixation element and an attachment feature, in accordance with an embodiment.

Referring to FIG. 13, a flowchart of a method of fabricating a biostimulator having low-polarization coatings on an inner fixation element and an attachment feature is shown in accordance with an embodiment. Similar to the fabrication of the attachment feature 450, the low-polarization coating may be applied to the inner fixation element 606 prior to integrating the subcomponent into the biostimulator 300. At operation 1302, the low-polarization coating, which may be a first low-polarization coating in the manufacturing process, may be disposed on the cathode 604. The cathode 604 may be the inner fixation element 606, and thus, the low-polarization coating can be applied to the outer surface 628 of the inner fixation element 606. It will be appreciated, however, that the cathode 604 may be a bulbous or dome-shaped electrode shape. More particularly, the low-polarization coating may be applied to any portion of the biostimulator 300 that acts as the cathode 604 to deliver the pacing pulses to the target tissue 302.

Application of the low-polarization coating to the cathode 604 may include several sub-operations. The first sub-operation can include sputtering a low-polarization material, such as titanium nitride, onto the outer surface 628 as a base layer. A second sub-operation can include platinizing the base layer to form a top layer. The electrode may be platinized by driving the electrode with a cathodic current in an aqueous solution. For example, the aqueous solution may be 0.072 molar chloroplatinic acid solution with about 0.00013 molar lead acetate. This can be an aqueous solution of about 2.92% chloroplatinic acid with about 0.044% lead acetate. The counter electrode or anode that is used in the platinization process may be platinum. The applied currents may be in a range of 10 milliamp/cm$^2$ for a total of 330 milliamp-sec/cm$^2$. The described process is provided by way of example only, however, and other processes may be used to provide platinization that yields favorable performance of the cathode 604. More particularly, the low-polarization coating on the cathode 604 can be formed by one or more sub-operations to render the true surface area of the cathode 604 sufficiently large to reduce the electrode polarization 104.

At operation 1304, the inner fixation element 606 is mounted on the housing 608, or another portion of the enclosure or the body of the biostimulator 300. The mounting operation can occur after disposing the low-polarization coating on the outer surface 628. Performing the mounting at that stage is convenient because coating the inner fixation element 606 after it is integrated into the biostimulator 300 may be difficult. As described above, the inner fixation element 606 can be coupled to the cup 1206 that is attached to the helix mount 1203. The helix mount 1203 can in turn be screwed onto the flange 1205 of the header assembly 620, and the header assembly 620 may then be mounted on a distal end of the housing 608 and welded thereto. Accordingly, the inner fixation element 606 can be indirectly mounted on the housing 608 at operation 1304.

At operation 1306, the outer fixation element 622 is mounted on the housing 608. Like the inner fixation element 606, the outer fixation element 622 can be indirectly mounted on the housing 608. For example, the outer fixation element 622 can be screwed onto the helix mount 1203, which is coupled to the housing 608 via the flange 1205 of the header assembly 620. The flange 1205 may be secured to the distal end of the housing 608 by a weld, e.g., a laser weld, extending circumferentially around the housing 608 and flange 1205. Accordingly, after operation 1306, a distal portion of the biostimulator 300 including the housing 608 and the header assembly 620 may be assembled.

At operation 1308, formation of a proximal portion of the biostimulator 300 may be initiated by disposing a second low-polarization coating on the exterior surface 626 of the attachment feature 450. Operation 1308 may be equivalent to operation 1102 described above. For example, the low-polarization coating can be a titanium nitride coating applied to the attachment feature 450 at the subcomponent level.

At operation 1310, the attachment feature 450 can be mounted on the proximal end of the cell can 618 after the low-polarization coating is applied to the exterior surface 626. The attachment feature 450 can be secured to the cell can 618 via the weld 624, as described above. Accordingly, after operation 1310, the proximal portion of the biostimulator 300 including the attachment feature 450 and the battery assembly 616 may be assembled.

At operation 1312, the housing 608 can be mounted on the distal end of the cell can 618. The proximal end of the housing 608 can mate to the distal end of the cell can 618, and a weld may be formed circumferentially around the housing 608 and the cell can 618 to secure the components. When the housing 608 is mounted on the cell can 618, the feedthrough pins of the battery assembly 616 may connect to corresponding connectors of the electronics within the electronics compartment 614. Accordingly, assembly of the biostimulator 300 may be complete with the battery assembly 616 capable of powering the electronics to deliver a pacing pulse through the inner fixation element 606 to the target tissue 302.

A biostimulator 300 having the features described above can be used to pace the target tissue 302. Immediately after pacing, the biostimulator sensing circuitry can perform capture verification by sensing the atrial evoked response potential between the cathode 604 and the anode 602. The low-polarization electrodes of the biostimulator 300 allow for atrial autocapture based on the detected evoked response. More particularly, the sensing system can use a discriminating means to discriminate the atrial evoked response 102. Discrimination of the atrial evoked response 102 can be performed by simple analog or digital algorithms that use the detected atrial evoked response, simple digital differentiation of the atrial evoked response, or simple digital integration of the atrial evoked response. More particularly, the detected signal 206, the first derivative of the detected signal, or the integral of the detected signal can be compared to a threshold to discriminate whether the atrium has been captured.

Figure 14:
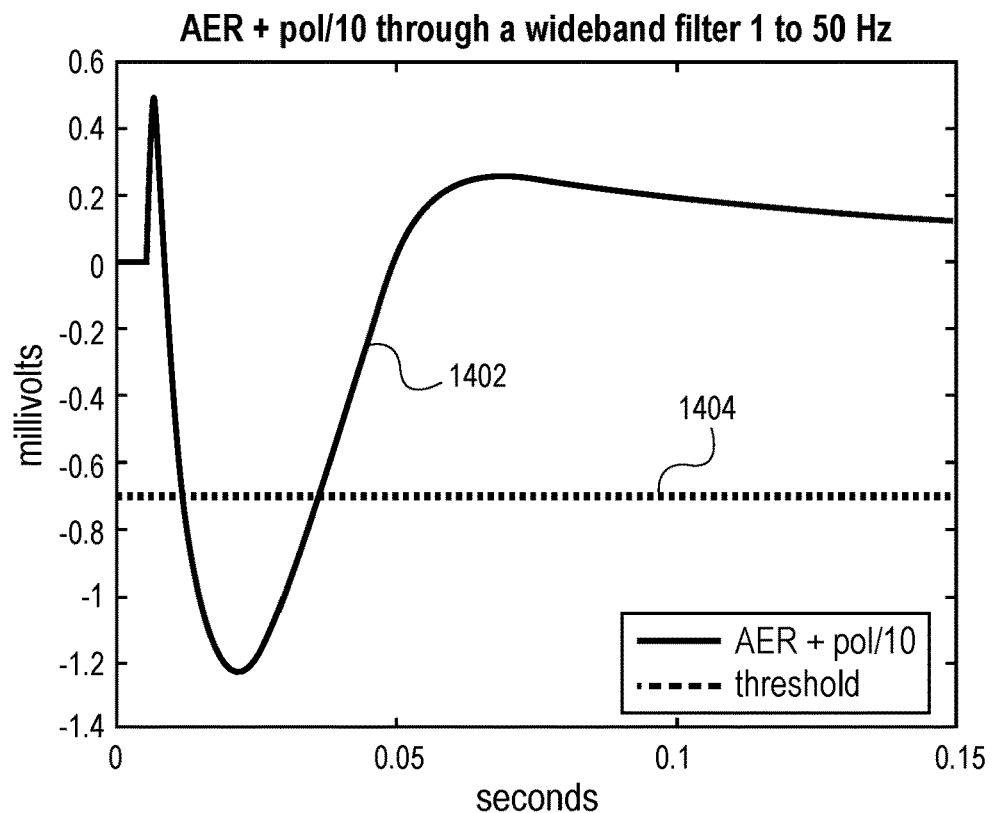
FIG. 14 is a graph of an atrial evoked response waveform and an electrode polarization waveform that have gone through a wideband filter, in accordance with an embodiment.

Referring to FIG. 14, a graph of an atrial evoked response waveform and an electrode polarization waveform that have gone through a wideband filter is shown in accordance with an embodiment. A filtered detected signal 1402 can be detected by the sensing system between the cathode 604 and the anode 602. The filtered detected signal 1402 represents the combined atrial evoked response 102 and the electrode polarization 104 signal, e.g., detected signal 206, that have been passed through a wideband filter. For example, the wideband filter can have a bandpass of 1 to 50 Hz. The polarization of the electrodes is reduced by the structure described above. For example, the anode 602 and the cathode 604 may be treated with respective low-polarization coatings to reduce the electrode polarization 104 by an order of magnitude from 5 mV to 0.5 mV. Accordingly, the basic shape of the atrial evoked response 102 is preserved in the filtered detected signal 1402. The filtered detected signal 1402 may be compared to a threshold 1404 by one or more processors of the biostimulator 300 executing a simple threshold detector algorithm. For example, if the filtered detected signal 1402 drops below a threshold 1404 of −0.7 mV, the processor(s) can determine that atrial capture has occurred.

Figure 15:
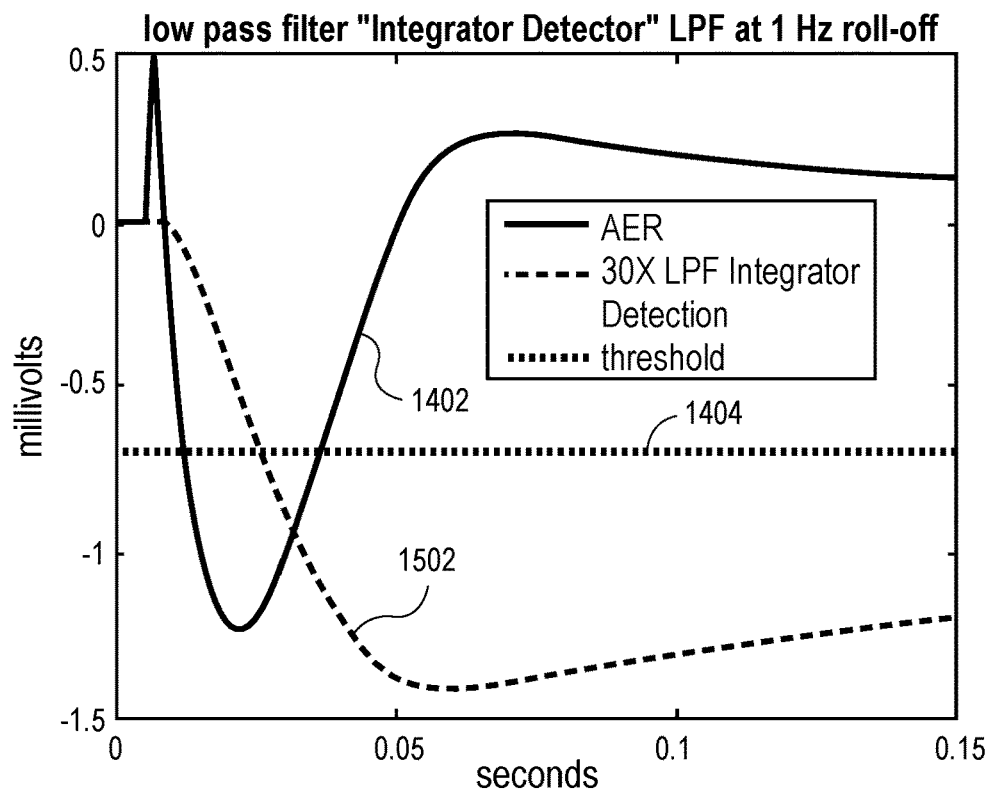
FIG. 15 is a graph of an atrial evoked response waveform and an electrode polarization waveform that have gone through a low pass filter and differentiation, in accordance with an embodiment.

Referring to FIG. 15, a graph of an atrial evoked response waveform and an electrode polarization waveform that have gone through a low pass filter and differentiation is shown in accordance with an embodiment. The processor(s) of the biostimulator 300 can implement simple integration to discriminate the atrial evoked response 102. The detected signal 206 combining the atrial evoked response 102 and the electrode polarization 104 may be passed through a low-pass filter with a high-frequency cut off and a predetermined gain to generate the filtered detected signal 1402. For example, the high-frequency cut off can be 1 Hz, and the predetermined gain can be 30×. Using the biostimulator 300 having low-polarization electrodes as described above, the biostimulator 300 can detect an integrated evoked response 1502. The integrated evoked response 1502 may be determined by the processor(s) of the biostimulator 300 using simple analog or digital algorithms to integrate the filtered detected signal 1402. The processor(s) can compare the integrated evoked response 1502 to the threshold 1404 to confirm atrial capture. For example, if the integrated evoked response 1502 drops below a threshold 1404 of −0.7 mV, the processor(s) can determine that atrial capture has occurred. Alternatively, the biostimulator 300 may use an analog-to-digital converter to digitize the detected signal 206 and sum the points of the digitized signal. Assuming that the atrial evoked response 102 is sampled at 256 Hz, this may require very few, e.g., 13, summations, and can therefore be performed with low processing power.

Figure 16:
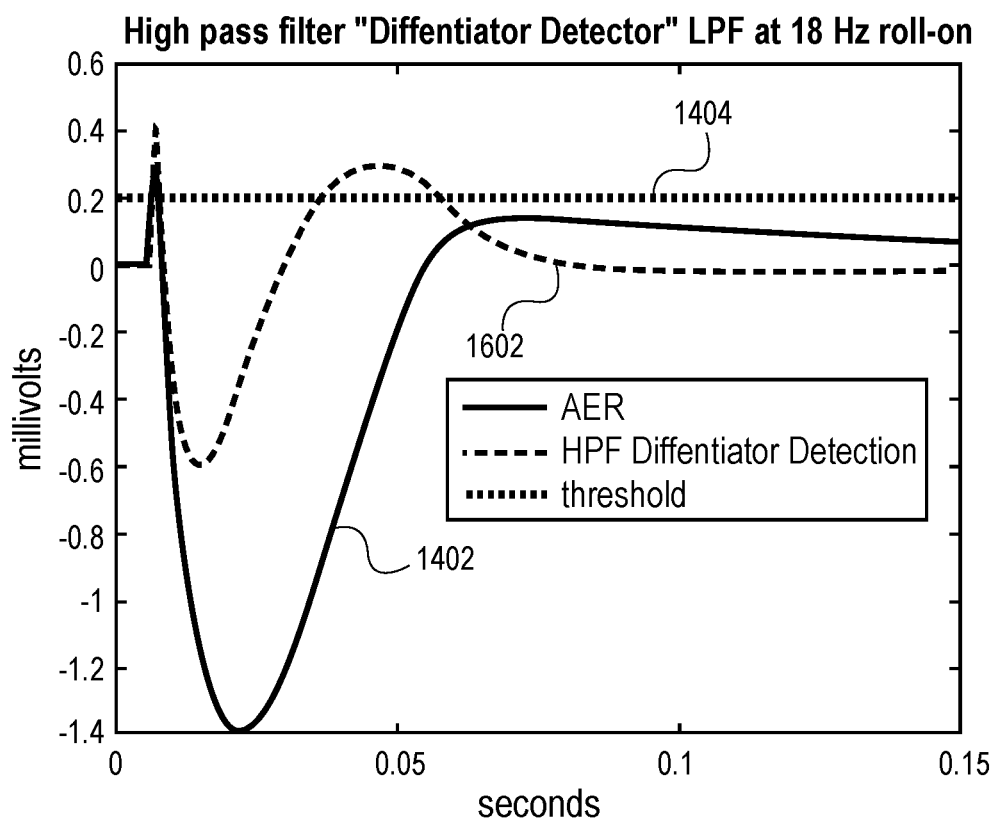
FIG. 16 is a graph of an atrial evoked response waveform and an electrode polarization waveform that have gone through a high pass filter and integration, in accordance with an embodiment.

Referring to FIG. 16, a graph of an atrial evoked response waveform and an electrode polarization waveform that have gone through a high pass filter and integration is shown in accordance with an embodiment. The processor(s) of the biostimulator 300 can implement simple differentiation to discriminate the atrial evoked response 102. The detected signal 206 combining the atrial evoked response 102 and the electrode polarization 104 may be passed through a high pass filter with a predetermined low-frequency roll-on to generate the filtered detected signal 1402. For example, the low-frequency cut off can be 1 Hz, and the predetermined low-frequency roll-on can be 18 Hz. Using the biostimulator 300 having low-polarization electrodes as described above, the biostimulator 300 can detect a differentiated evoked response 1602. The differentiated evoked response 1602 may be determined by the processor(s) of the biostimulator 300 using simple analog or digital algorithms to differentiate the filtered detected signal 1402. The processor(s) can compare the differentiated evoked response 1602 to the threshold 1404 to confirm atrial capture. For example, if the differentiated evoked response 1602 exceeds a threshold 1404 of 0.2 mV, the processor(s) can determine that atrial capture has occurred. Alternatively, the biostimulator 300 may use an analog-to-digital converter to digitize the detected signal 206 and take differences between pairs of points. Assuming that the atrial evoked response 102 is sampled at 256 Hz, this may require very few, e.g., 13, subtractions, and can therefore be performed with low processing power. A negative detection threshold 1404 could be used for comparison against the differentiated evoked response 1602, however, it is contemplated that the positive derivative detection may be more reliable.

Based on the data described above, it has been shown that low-polarization coating(s) on the electrode(s) of the biostimulator 300 can reduce electrode polarization such that simple signal processing techniques, including direct signal comparison, differentiation and comparison, or integration and comparison, can be used to reliably detect the atrial evoked response (or another chamber or tissue evoked response). Accordingly, the biostimulator 300 having the structure and configuration described above can perform autocapture without overburdening battery capacity. Thus, the described biostimulator 300 can reliably pace the heart over long periods of time.

In the foregoing specification, the invention has been described with reference to specific exemplary embodiments thereof. It will be evident that various modifications may be made thereto without departing from the broader spirit and scope of the invention as set forth in the following claims. The specification and drawings are, accordingly, to be regarded in an illustrative sense rather than a restrictive sense.

What is claimed is:

1. A biostimulator comprising:
   a battery assembly including a cell can containing an electrolyte;
   an attachment feature coupled to the battery assembly, wherein the attachment feature includes a stem having an annular stem wall extending around an internal cavity, wherein the stem extends between a base and a button, wherein the button includes a proximal button face having a face port extending into the internal cavity, and wherein the button includes an exterior surface and an interior surface around the internal cavity; and
   a low-polarization coating on the exterior surface and on a portion of the interior surface of the button, wherein the low-polarization coating effectively enlarges an electrode surface area of the button.

2. The biostimulator of claim 1, wherein the low-polarization coating includes one or more of titanium nitride or iridium oxide.

3. The biostimulator of claim 1, wherein the low-polarization coating covers an entirety of the exterior surface.

4. The biostimulator of claim 1, wherein the low-polarization coating covers the exterior surface and only the portion of the interior surface.

5. The biostimulator of claim 1, wherein the attachment feature is coupled to the battery assembly by a weld extending circumferentially around the base and the cell can.

6. The biostimulator of claim 1 further comprising an insulating coating on the cell can.

7. The biostimulator of claim 1, wherein the attachment feature is monolithically formed from a rigid material, and wherein the stem is a single post having an annular transverse profile.

8. The biostimulator of claim 1, wherein the attachment feature is an anode of the biostimulator.

9. A biostimulator system, comprising:
   a transport system including a catheter having a distal end; and
   a biostimulator coupled to the distal end and including
   a battery assembly including a cell can containing an electrolyte,
   an attachment feature coupled to the battery assembly, wherein the attachment feature includes a stem having an annular stem wall extending around an internal cavity, wherein the stem extends between a base and a button, and wherein the button includes a proximal button face having a face port extending into the internal cavity, and wherein the button includes an exterior surface and an interior surface around the internal cavity, and
   a low-polarization coating on the exterior surface and on a portion of the interior surface of the button, wherein the low-polarization coating effectively enlarges an electrode surface area of the button.

10. The biostimulator system of claim 9, wherein the low-polarization coating includes one or more of titanium nitride or iridium oxide.

11. The biostimulator system of claim 9, wherein the low-polarization coating covers an entirety of the exterior surface.

12. The biostimulator system of claim 9, wherein the low-polarization coating covers the exterior surface and only the portion of the interior surface.

13. The biostimulator system of claim 9, wherein the attachment feature is coupled to the battery assembly by a weld extending circumferentially around the base and the cell can.

14. The biostimulator of claim 9, wherein the attachment feature is an anode of the biostimulator.

15. A method, comprising:
   disposing a low-polarization coating on a button of an attachment feature, wherein the attachment feature includes a stem having an annular stem wall extending around an internal cavity, wherein the stem extends between a base and the button, wherein the low-polarization coating effectively enlarges an electrode surface area of the button, wherein the button includes a proximal button face having a face port extending into the internal cavity, and wherein the button includes an exterior surface and an interior surface around the internal cavity; and
   mounting the attachment feature on a battery assembly after disposing the low-polarization coating on the exterior surface and on a portion of the interior surface of the button, wherein the battery assembly includes a cell can containing an electrolyte.

16. The method of claim 15, wherein the low-polarization coating includes one or more of titanium nitride or iridium oxide.

17. The method of claim 15, wherein the low-polarization coating covers an entirety of the exterior surface of the attachment feature.

18. The method of claim 15, wherein the low-polarization coating covers the exterior surface and only the portion of the interior surface.

19. The method of claim 15 further comprising welding the attachment feature to the battery assembly circumferentially around the base and the cell can.

20. The method of claim 15 further comprising disposing an insulating coating on the cell can.

* * * * *